US012797044B2

(12) United States Patent
Yu et al.

(10) Patent No.: US 12,797,044 B2
(45) Date of Patent: Nov. 17, 2026

(54) ACCELERATED COUPLED FILTERING METHOD AND SYSTEM FOR TISSUE DEFORMATION ANALYSIS

(71) Applicant: The Hong Kong University of Science and Technology, Hong Kong (CN)

(72) Inventors: Weichuan Yu, Hong Kong (CN); Jingwen Zheng, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 14 days.

(21) Appl. No.: 19/084,991

(22) Filed: Mar. 20, 2025

(65) Prior Publication Data

US 2025/0295393 A1 Sep. 25, 2025

Related U.S. Application Data

(60) Provisional application No. 63/567,427, filed on Mar. 20, 2024.

(51) Int. Cl.
*A61B 8/00* (2006.01)

(52) U.S. Cl.
CPC .......... *A61B 8/5269* (2013.01); *A61B 8/5246* (2013.01)

(58) Field of Classification Search
CPC ... A61B 8/5223; A61B 8/5246; A61B 8/5269; A61B 8/5276
See application file for complete search history.

(56) References Cited

U.S. PATENT DOCUMENTS 9,286,691 B2 3/2016 Yu et al.
9,390,514 B2 7/2016 Yu et al.
(Continued)

FOREIGN PATENT DOCUMENTS

WO WO-2017144716 A1 * 8/2017 ......... G01S 7/52077

OTHER PUBLICATIONS

Jianwen Luo et al., A fast normalized cross-correlation calculation method for motion estimation. IEEE Trans. Ultrason. Ferroelectr. Freq. Control. 2010, 57(6); pp. 1347-1357.

*Primary Examiner* — Christopher L Cook
(74) *Attorney, Agent, or Firm* — S&F/WEHRW

(57) ABSTRACT

There is provided an accelerated coupled filtering method for tissue deformation analysis. The method includes steps of applying, by a processing device, a first filter on a pre-deformation image of a tissue to obtain a filtered pre-deformation image, and applying, by the processing device, a second filter on a post-deformation image of the tissue to obtain a filtered post-deformation image. The filtered pre-deformation image and the filtered post-deformation image can be correlated by a first motion matrix including a plurality of first motion parameters. The plurality of first motion parameters can include at least three fundamental first motion parameters, each of the three fundamental first motion parameters can represent movement of the tissue along an axial direction relative to the axial direction, an elevational direction and a lateral direction, respectively. The method further includes a step of estimating, by the processing device, a respective value for each of the plurality of first motion parameters. Each of the estimated respective values can represent a difference between the pre-deformation and post-deformation filtered images. The method further includes a step of, in response to determining that at least one of the estimated respective values meets at least one predefined criterion, updating the at least one of the estimated respective values as an optimal value for at least one corresponding first motion parameter of the plurality of first motion parameters.

14 Claims, 21 Drawing Sheets

(56) References Cited

U.S. PATENT DOCUMENTS

| | | | | |
|---|---|---|---|---|
| 2018/0132830 | A1* | 5/2018 | Mahmoud | A61B 5/0059 |
| 2022/0292637 | A1* | 9/2022 | Huang | A61B 8/06 |

* cited by examiner

| Scale | | 1 | 2 | 3 | 4 | 5 | 6 |
|---|---|---|---|---|---|---|---|
| Step of $M$ | $m_{x*}, m_{y*}$ | 2.50E-2 | 1.25E-2 | 6.25E-3 | 6.25E-3 | 6.25E-3 | 6.25E-3 |
| | $m_{z*}$ | 2.50E-2 | 1.25E-2 | 6.25E-3 | 3.13E-3 | 1.56E-3 | 1.56E-3 |
| Size of $\mathbb{M}$ | $m_{zz}$ | 8 | 5 | 5 | 5 | 5 | 3 |
| | $m_{zx}$ | 4 | 5 | 5 | 5 | 5 | 3 |
| | $m_{*y}$ | 1 | 1 | 1 | 1 | 1 | 1 |
| | Others | 4 | 3 | 3 | 1 | 1 | 1 |
| Step of $\boldsymbol{T}$ | $t_x, t_y$ | 2 | 1 | 1 | 1 | 1 | 1 |
| | $t_z$ | 2 | 1 | 1 | 1 | 1 | 0.5 |
| Size of $\mathbb{T}$ | $t_x, t_y$ | 11 | 5 | 5 | 5 | 3 | 1 |
| | $t_z$ | 79 | 5 | 5 | 5 | 5 | 5 |

Fig. 3

| Method | Time Complexity | | Space Complexity | | Estimated FLOPs ↓ | |
|---|---|---|---|---|---|---|
| | 2D | 3D | 2D | 3D | 2D | 3D |
| (a) | $O[n_i^4 n_b^2 n_m^3]$ | $O[n_i^6 n_b^3 n_m^8]$ | $O[n_i^2]$ | $O[n_i^3]$ | 1.67E+17 | 1.63E+28 |
| (a)+(b) (baseline) | $O[n_i^2 n_b^2 n_m^3]$ | $O[n_i^3 n_b^3 n_m^8]$ | $O[n_i^2]$ | $O[n_i^3]$ | 5.36E+14 | 2.36E+24 |
| (a)+(b)+(c) | $O[n_i^2 n_b^2 n_m^3]$ | $O[n_i^3 n_b^3 n_m^6]$ | $O[n_i^2 n_a]$ | $O[n_i^3 n_a]$ | 1.22E+14 | 1.53E+19 |
| (a)+(b)+(c)+(d) | $O[n_i^2 n_b^2 \log(n_b)]$ | $O[n_i^3 n_b^3 \log(n_b)]$ | $O[n_i^2 n_a]$ | $O[n_i^3 n_a]$ | 8.07E+11 | 7.26E+14 |
| (a)+(b)+(c)+(d)+(e) (FastCF) | $O[n_i^2 n_b^2 \log(n_b)]$ | $O[n_i^3 n_b^3 \log(n_b)]$ | $O[n_i^2 n_a]$ | $O[n_i^3 n_a]$ | 6.92E+11 | 5.59E+14 |

Fig. 10

| Parameter | 2D | 3D |
|---|---|---|
| Size of input image $I_A, I_B$ in #voxels | $n_i^2$ | $n_i^3$ |
| Number of iterations/ resolution levels | $n_s$ | $n_s$ |
| Number of elements in $\mathbb{V}$ or Size of output $I_E$ | $n_o^2 \approx n_i^2$ | $n_i^3$ |
| Size of block in #voxels | $n_b^2 \ll n_i^2$ | $n_i^3$ |
| Size of point spread function in #voxels | $n_p^2 \approx n_b^2$ | $n_b^3$ |
| Number of elements in $\mathbb{M}$ | $n_m^{(2\times2-1)}$ | $n_m^8$ |
| Number of elements in $\mathbb{T}$ | $n_t^2 \approx n_i^2$ | $n_i^3$ |
| Number of concurrently processed blocks | $n_a$ | $n_a$ |

Fig. 11

| Methods | Scale | Steps | | |
|---|---|---|---|---|
| | | Coupled Filtering | Envelope Detection | Block Matching |
| (a) | N/A | $O[n_i^3 \log(n_i)\, n_m^8]$ | N/A | $O[n_i^6 n_b^3 n_m^8]$ |
| (a)+(b) (baseline) | 1 | $O[n_i^3 \log(n_i)\, n_m^8]$ | N/A | $O[n_i^3 n_b^3 n_m^8]$ |
| | 2-5 | $\ll O[n_i^3 \log(n_i)\, n_m^8]$ | N/A | $\ll O[n_i^3 n_b^3 n_m^8]$ |
| | 6 | $O[n_i^3 n_b^3 \log(n_b)]$ | N/A | $O[n_i^3 n_b^3]$ |
| (a)+(b)+(c) | 1 | $O[n_i^3 \log(n_i)\, n_m^2]$ | N/A | $O[n_i^3 n_b^3 n_m^6]$ |
| | 2-5 | $\ll O[n_i^3 \log(n_i)\, n_m^2]$ | N/A | $\ll O[n_i^3 n_b^3 n_m^6]$ |
| | 6 | $O[n_i^3 n_b^3 \log(n_b)$ | N/A | $O[n_i^3 n_b^3]$ |
| (a)+(b)+(c)+(d) | 1 | $O[n_i^3 \log(n_i)]$ | $O[n_i^3 \log(n_i)]$ | $O[n_i^3 n_b^2]$ |
| (a)+(b)+(c)+(d) +(e) (FastCF) | 2-5 | $\le O[n_i^3 n_b^3 \log(n_b)]$ | N/A | $\le O[n_i^3 n_b^3]$ |
| | 6 | $O[n_i^3 n_b^3 \log(n_b)]$ | N/A | $O[n_i^3 n_b^3]$ |

Fig. 12

| Scale | 1 | 2 | 3 | 4 | 5 | 6 | Total |
|---|---|---|---|---|---|---|---|
| SRMSE (CPU) ↓ | 1.946 | 0.907 | 0.822 | 0.845 | 0.630 | 0.602 | N/A |
| Time (s) (CPU) ↓ | 242 | 69 | 329 | 623 | 241 | 1075 | 2589 |

Fig. 13

| Function | Time (s) (CPU) ↓ |
|---|---|
| Coupled Filtering | 1879 |
| ----Data Preparation | 304 |
| ----Fourier Transform | 1470 |
| ----Freq. Domain Multiplication | 106 |
| Block Matching | 322 |
| ----Interpolation | 170 |
| ----Calculate Metric & find best | 152 |
| Post-processing | 1.8 |
| Others | 399 |

Fig. 15

| Options \ Scale | 1 | 2 | 3 | 4 | 5 | 6 |
|---|---|---|---|---|---|---|
| Veryslow | 1.825 | 0.821 | 0.817 | 0.853 | 0.637 | 0.608 |
| Slower | 2.231 | 0.828 | 0.811 | 0.846 | 0.649 | 0.609 |
| Slow | 1.781 | 0.847 | 0.830 | 0.865 | 0.624 | 0.609 |
| Medium | 2.062 | 1.086 | 0.979 | 0.981 | 0.805 | 0.784 |
| FastCF | **1.946** | **0.907** | **0.822** | **0.845** | **0.630** | **0.602** |

Fig. 19

ACCELERATED COUPLED FILTERING METHOD AND SYSTEM FOR TISSUE DEFORMATION ANALYSIS

CROSS-REFERENCE TO RELATED APPLICATIONS

The present application claims priority from U.S. Provisional Patent Application No. 63/567,427, filed on Mar. 20, 2024, which is hereby incorporated by reference in its entirety.

FIELD OF INVENTION

The present invention relates broadly, but not exclusively, to accelerated coupled filtering methods and systems for tissue deformation analysis.

BACKGROUND

Ultrasound image-based tissue deformation analysis can be used to measure tissue stiffness and reveal useful information for clinical diagnosis. Such analysis is typically performed by comparing images taken before and after deformation of tissues. However, feature motion decorrelation caused by the ultrasound imaging procedure can greatly impede accuracy. To address this problem, a coupled filtering method was proposed and implemented to compensate for feature motion decorrelation analytically. Although the coupled filtering method can achieve much higher accuracy as compared to other existing methods, such method is computationally expensive. Thus, the implementation of such method is typically limited to two-dimensional (2D) analysis. In order to obtain a complete tissue deformation analysis, it is necessary to extend the implementation of the coupled filtering method to three-dimensional (3D) analysis. However, doing so will require billions of times more operations than the 2D implementation, which makes the 3D implementation impractical for real-world applications.

Therefore, a need exists to provide accelerated coupled filtering methods and systems for tissue deformation analysis.

SUMMARY

According to a first aspect of the present invention, there is provided an accelerated coupled filtering method for tissue deformation analysis. The method includes applying, by a processing device, a first filter on a pre-deformation image of a tissue to obtain a filtered pre-deformation image; applying, by the processing device, a second filter on a post-deformation image of the tissue to obtain a filtered post-deformation image, the filtered pre-deformation image and the filtered post-deformation image are correlated by a first motion matrix comprising a plurality of first motion parameters, and the plurality of first motion parameters include at least three fundamental first motion parameters, each of the three fundamental first motion parameters represents movement of the tissue along an axial direction relative to the axial direction, an elevational direction and a lateral direction, respectively; estimating, by the processing device, a respective value for each of the plurality of first motion parameters, each of the estimated respective values represent a difference between the pre-deformation and post-deformation filtered images; and in response to determining that at least one of the estimated respective values meets at least one predefined criterion, updating the at least one of the estimated respective values as an optimal value for at least one corresponding first motion parameter of the plurality of first motion parameters.

In embodiments of the present disclosure, applying the first filter and the second filter may include convolving a first point spread function and second point spread function of an ultrasound system with the pre-deformation image and the post-deformation image, respectively, and the first point spread function may be a modified version of the second point spread function.

In embodiments of the present disclosure, after applying the second filter, the method may include a step of spatially transforming, by the processing device, the post-deformation image based at least on a second motion matrix. The first motion matrix may be a modified version of the second motion matrix.

In embodiments of the present disclosure, the method may include a step of detecting, by the processing device, one or more envelopes present in the filtered pre-deformation image and filtered post-deformation image to obtain a filtered B-mode pre-deformation image and a filtered B-mode post-deformation image.

In embodiments of the present disclosure, the filtered pre-deformation image and filtered post-deformation image may be 3-dimensional (3D) images, and estimating the respective values may include (A) flattening, by the processing device, a first and second plurality of voxels surrounding each of one or more pre-deformation points of interest in the filtered pre-deformation image and each of one or more post-deformation points of interest in the filtered post-deformation image, respectively. The flattening may be performed along the elevational direction of each of the first and second plurality of voxels, and the flattening may reduce the plurality of first and second motion parameters.

In embodiments of the present disclosure, estimating the respective values may be performed in a plurality of iterations. In a first iteration of the plurality of iterations, the plurality of first motion parameters may include two of the three fundamental first motion parameters representing movement of the tissue along the axial direction relative to the axial direction and the lateral direction, respectively. The remaining fundamental first motion parameter may be removed by the flattening. Between a second iteration to a final iteration of the plurality of iterations, the plurality of first motion parameters may include the two of the three fundamental first motion parameters, two lateral first motion parameters representing movement of the tissue along the lateral direction relative to the lateral direction and the axial direction, respectively, and two elevational first motion parameters representing movement of the tissue along the elevational direction relative to the lateral direction and the axial direction, respectively.

In embodiments of the present disclosure, the second motion matrix may include a plurality of second motion parameters. Estimating the respective values may further include (B) searching, by the processing device, a value of each of the plurality of first motion parameters for each of the one or more pre-deformation points of interest in the filtered pre-deformation image; (C) searching, by the processing device, a value of each of the plurality of second motion parameters for each of the one or more post-deformation points of interest in the filtered post-deformation image; (D) generating, by the processing device, one or more pre-deformation voxels based on the searched value of each of the plurality of first motion parameters; (E) generating, by the processing device, one or more post-deformation voxels based on the searched value of each of the plurality of second motion parameters; (F) calculating, by the processing device, a similarity metric based on one or more first voxels surrounding the one or more pre-deformation voxels and one or more second voxels surrounding the one or more post-deformation voxels, the similarity metric may define a similarity between a target pre-deformation point of interest and a post-deformation point of interest corresponding to the target pre-deformation point of interest; and (G) determining, by the processing device, if the target pre-deformation point of interest matches the corresponding post-deformation point of interest based on the calculated similarity metric.

In embodiments of the present disclosure, the plurality of second motion parameters may include at least two fundamental second motion parameters, two lateral second motion parameters and two elevational motion parameters. Estimating the respective values may further include, in the first iteration, determining, by the processing device, a value of each of the two of the three fundamental first motion parameters based on steps (A) to (G); between the second iteration to a third final iteration, determining, by the processing device, an updated value of each of the two of the three fundamental first motion parameters based on steps (A) to (G), and assigning, by the processing device, a value of each of the two lateral second motion parameters and the two elevational second motion parameters searched in step (C) in a previous iteration as a respective value of each of the two lateral first motion parameters and the two elevational first motion parameters; and in a final two iterations, assigning, by the processing device, the determined updated value of each of the two of the three fundamental first motion parameters in the third final iteration as an optimal value of each of the two of the three fundamental first motion parameters, and assigning, by the processing device, an updated value of each of the two lateral second motion parameters and the two elevational second motion parameters searched in step (C) in the third final iteration as an optimal value of each of the two lateral first motion parameters and the two elevational first motion parameters.

In embodiments of the present disclosure, the similarity metric may include any one of a Normalized Correlation Coefficient, Sum of Absolute Differences and Sum of Squared Differences.

In embodiments of the present disclosure, the method may further include imposing, by the processing device, an upper limit and a lower limit on a gradient of a displacement range of the fundamental first motion parameters along the axial direction, values falling outside the displacement range may be determined to be a wrong value of the fundamental first motion parameters; in response to determining that one or more voxels include the wrong value of the fundamental first motion parameters, determining, by the processing device, a corrected value of the fundamental first motion parameters of the one or more voxels, the corrected value may be determined by interpolating the wrong value based on a predetermined correct value of the fundamental first motion parameters of voxels surrounding the one or more voxels.

According to a second aspect of the present invention, there is provided a system for performing an accelerated coupled filtering method for tissue deformation analysis, the system includes a processing device configured to: apply a first filter on a pre-deformation image of a tissue to obtain a filtered pre-deformation image; apply a second filter on a post-deformation image of the tissue to obtain a filtered post-deformation image, the filtered pre-deformation image and the filtered post-deformation image are correlated by a first motion matrix including a plurality of first motion parameters, and the plurality of first motion parameters include at least three fundamental first motion parameters, each of the three fundamental first motion parameters represents movement of the tissue along an axial direction relative to the axial direction, an elevational direction and a lateral direction, respectively; estimate a respective value for each of the plurality of first motion parameters, each of the estimated respective values represent a difference between the pre-deformation and post-deformation filtered images; and in response to determining that at least one of the estimated respective values meets at least one predefined criterion, update the at least one of the estimated respective values as an optimal value for at least one corresponding first motion parameter of the plurality of first motion parameters.

In embodiments of the present disclosure, applying the first filter and the second filter may include: convolve a first point spread function and second point spread function of an ultrasound system with the pre-deformation image and the post-deformation image, respectively, and the first point spread function may be a modified version of the second point spread function.

In embodiments of the present disclosure, after applying the second filter, the system may be configured to: spatially transform the post-deformation image based at least on a second motion matrix. The first motion matrix may be a modified version of the second motion matrix.

In embodiments of the present disclosure, the processing device may be configured to detect one or more envelopes present in the filtered pre-deformation image and filtered post-deformation image to obtain a filtered B-mode pre-deformation image and a filtered B-mode post-deformation image.

In embodiments of the present disclosure, the filtered pre-deformation image and filtered post-deformation image may be 3-dimensional (3D) images, and to estimate the respective values, the processing device may be configured to: (A) flatten a first and second plurality of voxels surrounding each of one or more pre-deformation points of interest in the filtered pre-deformation image and each of one or more post-deformation points of interest in the filtered post-deformation image, respectively. The flattening may be performed along the elevational direction of each of the first and second plurality of voxels, and the flattening may reduce the plurality of first and second motion parameters.

In embodiments of the present disclosure, estimating the respective values may be performed in a plurality of iterations. In a first iteration of the plurality of iterations, the plurality of first motion parameters may include two of the three fundamental first motion parameters representing movement of the tissue along the axial direction relative to the axial direction and the lateral direction, respectively. The remaining fundamental first motion parameter may be removed by the flattening. Between a second iteration to a final iteration of the plurality of iterations, the plurality of first motion parameters may include the two of the three fundamental first motion parameters, two lateral first motion parameters representing movement of the tissue along the lateral direction relative to the lateral direction and the axial direction, respectively, and two elevational first motion parameters representing movement of the tissue along the elevational direction relative to the lateral direction and the axial direction, respectively.

In embodiments of the present disclosure, the second motion matrix may include a plurality of second motion parameters. Further, to estimate the respective values, the processing device may be further configured to: (B) search a value of each of the plurality of first motion parameters for each of the one or more pre-deformation points of interest in the filtered pre-deformation image; (C) search a value of each of the plurality of second motion parameters for each of the one or more post-deformation points of interest in the filtered post-deformation image; (D) generate one or more pre-deformation voxels based on the searched value of each of the plurality of first motion parameters; (E) generate one or more post-deformation voxels based on the searched value of each of the plurality of second motion parameters; (F) calculate a similarity metric based on one or more first voxels surrounding the one or more pre-deformation voxels and one or more second voxels surrounding the one or more post-deformation voxels, the similarity metric may define a similarity between a target pre-deformation point of interest and a post-deformation point of interest corresponding to the target pre-deformation point of interest; and (G) determine if the target pre-deformation point of interest matches the corresponding post-deformation point of interest based on the calculated similarity metric.

In embodiments of the present disclosure, the plurality of second motion parameters may include at least two fundamental second motion parameters, two lateral second motion parameters and two elevational motion parameters. To estimate the respective values, the processing device may be further configured to: in the first iteration, determine a value of each of the two of the three fundamental first motion parameters based on steps (A) to (G); between the second iteration to a third final iteration, determine an updated value of each of the two of the three fundamental first motion parameters based on steps (A) to (G), and assign a value of each of the two lateral second motion parameters and the two elevational second motion parameters searched in step (C) in a previous iteration as a respective value of each of the two lateral first motion parameters and the two elevational first motion parameters; and in a final two iterations, assign the determined updated value of each of the two of the three fundamental first motion parameters in the third final iteration as an optimal value of each of the two of the three fundamental first motion parameters, and assign an updated value of each of the two lateral second motion parameters and the two elevational second motion parameters searched in step (C) in the third final iteration as an optimal value of each of the two lateral first motion parameters and the two elevational first motion parameters.

In embodiments of the present disclosure, the similarity metric may include any one of a Normalized Correlation Coefficient, Sum of Absolute Differences and Sum of Squared Differences.

In embodiments of the present disclosure, the processing device may be configured to: impose an upper limit and a lower limit on a gradient of a displacement range of the fundamental first motion parameters along the axial direction, values falling outside the displacement range may be determined to be a wrong value of the fundamental first motion parameters; in response to determining that one or more voxels include the wrong value of the fundamental first motion parameters, determine a corrected value of the fundamental first motion parameters of the one or more voxels, the corrected value may be determined by interpolating the wrong value based on a predetermined correct value of the fundamental first motion parameters of voxels surrounding the one or more voxels.

BRIEF DESCRIPTION OF THE DRAWINGS

Embodiments of the invention will be better understood and readily apparent to one of ordinary skill in the art from the following written description, by way of example only, and in conjunction with the drawings, in which:

FIG. 3 shows a table listing parameters used in FastCF, in accordance with an embodiment.

FIG. 10 shows a table listing the time complexity, space complexity and estimated Floating-point Operations per second (FLOPs) for 2D and 3D implementations of various coupled filtering methods, in accordance with an embodiment.

FIG. 11 shows a table listing parameters used for the time complexity and space complexity analysis for the 2D and 3D implementations of the various coupled filtering methods, in accordance with an embodiment.

FIG. 12 shows another table listing detailed time complexity analysis for the 3D implementation of various coupled filtering methods, in accordance with an embodiment.

FIG. 13 shows a table listing the square root of mean square error (SRMSE) and computation time of FastCF performed on 3D simulated dataset, in accordance with an embodiment.

FIG. 15 shows a table listing computation time of different functions used in the FastCF process on the 3D simulated dataset, in accordance with an embodiment.

FIG. 19 shows a table listing SRMSE of FastCF under different setting options, in accordance with an embodiment.

DETAILED DESCRIPTION

Figure 1:
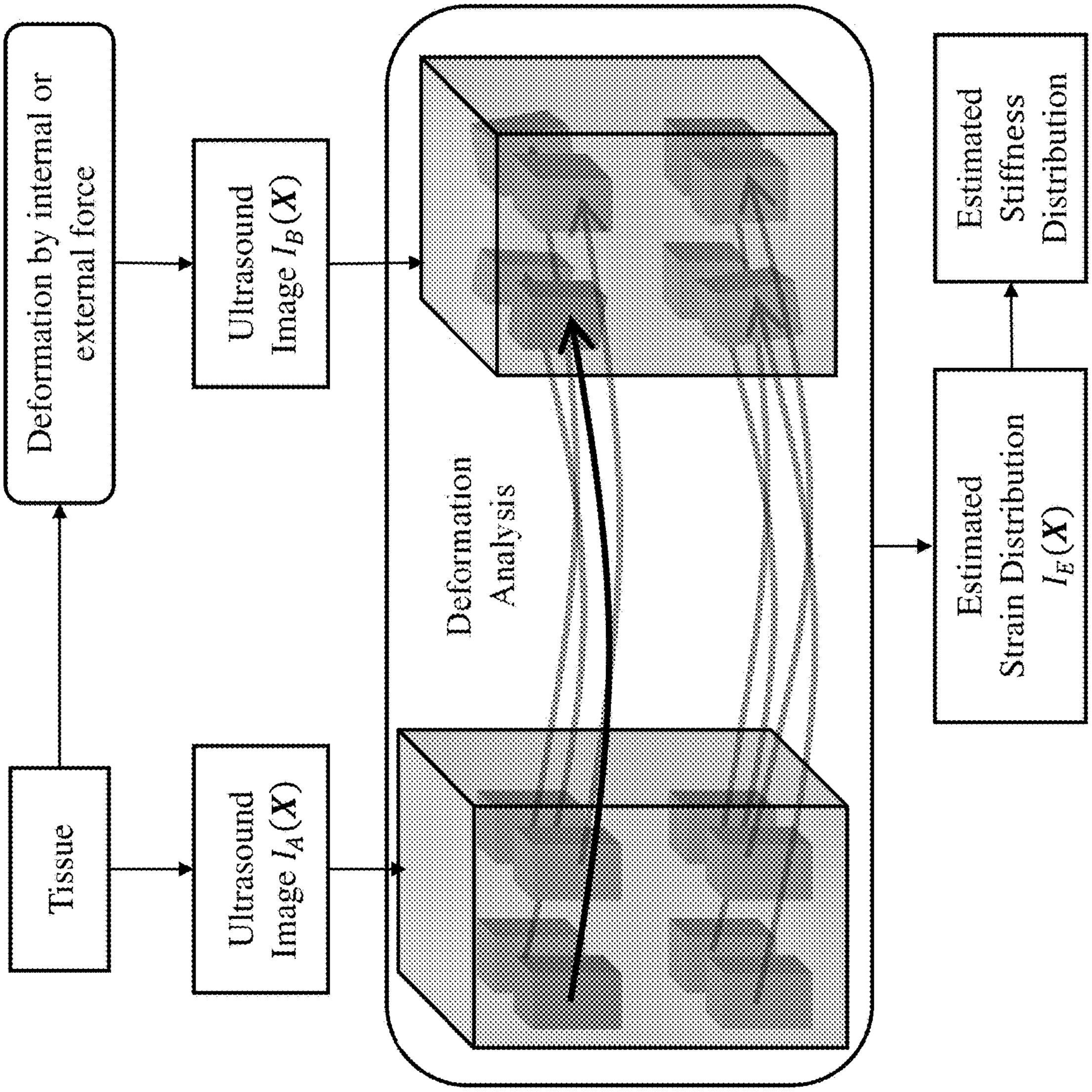
FIG. 1 shows a flowchart illustrating a conventional tissue deformation analysis process.

Embodiments of the present invention will be described, by way of example only, with reference to the drawings. Like reference numerals and characters in the drawings refer to like elements or equivalents.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "scanning", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a computer or other device selectively activated or reconfigured by a computer program stored in the computer. The algorithms and displays presented herein are not inherently related to any particular computer or other apparatus. Various machines may be used with programs in accordance with the teachings herein. Alternatively, the construction of more specialized apparatus to perform the required method steps may be appropriate. The structure of a conventional computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a computer. The computer readable medium may also include a hard-wired medium such as exemplified in the Internet system, or wireless medium such as exemplified in the GSM, GPRS, 3G or 4G mobile telephone systems, as well as other wireless systems such as Bluetooth, ZigBee, Wi-Fi. The computer program when loaded and executed on such a computer effectively results in an apparatus that implements the steps of the preferred method.

The present invention may also be implemented as hardware modules. More particularly, in the hardware sense, a module is a functional hardware unit designed for use with other components or modules. For example, a module may be implemented using discrete electronic components, or it can form a portion of an entire electronic circuit such as an Application Specific Integrated Circuit (ASIC) or Field Programmable Gate Array (FPGA). Numerous other possibilities exist. Those skilled in the art will appreciate that the system can also be implemented as a combination of hardware and software modules.

In the following description, the term "module" can refer to software, a hardware element, or a combination of both.

An Application Programming Interface (API) enables software and applications to communicate with each other. It is a software-to-software interface that allows for separate parties to communicate with each other without any previous user knowledge or intervention. In general terms, it is a set of clearly defined methods of communication between various software components.

This specification uses the term "configured to" in connection with systems, apparatus, and computer program components. For a system of one or more computers to be configured to perform particular operations or actions means that the system has installed on its software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions. For special-purpose logic circuitry to be configured to perform particular operations or actions means that the circuitry has electronic logic that performs the operations or actions.

As used herein, the term "processing device" refers to any hardware or system configured to perform computational tasks.

By way of examples, malignant tumours, cirrhotic liver, and dead heart tissues are significantly stiffer than healthy tissues. As such, stiffness can reveal pathologies, which led to doctors performing tissue deformation analysis to track the deformation induced by internal or external forces so as to deduce the stiffness distribution to facilitate diagnosis. FIG. 1 shows a flowchart illustrating a typical process of the tissue deformation analysis. For accurate tissue deformation analysis, coupled filtering method was proposed, which applies two different but coupled filters to images taken before and after tissue deformation, respectively, to compensate for both complex motion, i.e., feature motion decorrelation, and interference of echo waves. Adopting the coupled filtering method can result in a much higher accuracy than other relevant methods, especially for large tissue deformation. However, such method may require re-filtering of the images for different motions by exhaustively searching through all possible discrete motions. Consequently, such a heavy computational load makes only implementation on 2D images feasible in practical use, which may take around 45 hours to analyze a pair of images sized 201×1001 in MATLAB on the CPU and around 20 minutes on the FPGA.

Further, as tissues move in all directions, tissue deformation analysis is preferably performed on 3D images so that all motions can be examined to achieve high accuracy. Due to the exhaustive search for all possible affine motion, the 3D implementation of the coupled filtering method is estimated to perform billions more calculations than the 2D implementation. Therefore, the present disclosure seeks to improve the algorithmic complexity of the coupled filtering method. Specifically, the present disclosure provides a method that can accelerate the coupled filtering method while maintaining a similar accuracy (hereinafter referred to as "FastCF"). The main functions of FastCF are as follows: 1) approximating the motion can reduce the required amount of times that the coupled filters are applied, 2) employing envelope detection can reduce the search space of the motion parameters by heuristically refining the search for increased speed and 3) adding a quick post-processing step can compensate possible inaccuracies introduced by the approximation. In the following section, the conventional coupled filtering method is briefly described, of which this method serves as a foundation to FastCF.

Coupled Filtering Method and "Baseline Method"

The coupled filtering method can be, for example, designed to compensate for feature motion decorrelation. The ultrasound image before deformation, $I_A(X)$, can be modeled as:

$$I_A(X) = Z(X) * H(X), \tag{1}$$

where Z(X) represents scatterers, * denotes convolution, and H(X) represents the point spread function of the imaging system. Further, Z(X) and H(X) can be modelled as follows:

$$Z(X) = \sum\nolimits_{n=1}^{N} a_n \delta(X - p_n) \tag{1}$$

$$H(X) = \exp\left[-\frac{1}{2} X^T \Gamma X\right] \cos(2\pi X^T U_0) \tag{2}$$

Here, $$P = \{(a_1, p_1), (a_2, p_2), \cdots, (a_N, p_N)\} \tag{3}$$

where $a_1, \ldots, a_N$ denotes amplitudes of the scatterers and $p_1, \ldots, p_N$ denotes positions of the scatterers, X, $p_n \in \mathbb{R}^{3\times1}$ denote image coordinates and the positions of scatterers, respectively, N is the number of scatterers $$\Gamma = \text{diag}\left(\frac{1}{\sigma_x^2}, \frac{1}{\sigma_y^2}, \frac{1}{\sigma_z^2}\right)$$

where x, y, and z represent the lateral, elevational and axial directions, respectively, and $U_0 = [0\ 0\ u_z]^T$ are parameters for the point spread function.

Given the motion model:

$$X' = M(X + T), \tag{4}$$

-continued $$\text{with affine motion matrix } M = \begin{bmatrix} m_{xx} & m_{xy} & m_{xz} \\ m_{yx} & m_{yy} & m_{yz} \\ m_{zx} & m_{zy} & m_{zz} \end{bmatrix},$$

$$\text{and displacement vector } T = [t_x\ \ t_y\ \ t_z]^T.$$

The following equation can be derived, which describes the coupled filtering method:

$$I_A(X) * H(MX) = I_B[M(X + T)] * H(X) \tag{5}$$

where $I_B(X)$ is the image after deformation.

Figure 2A:
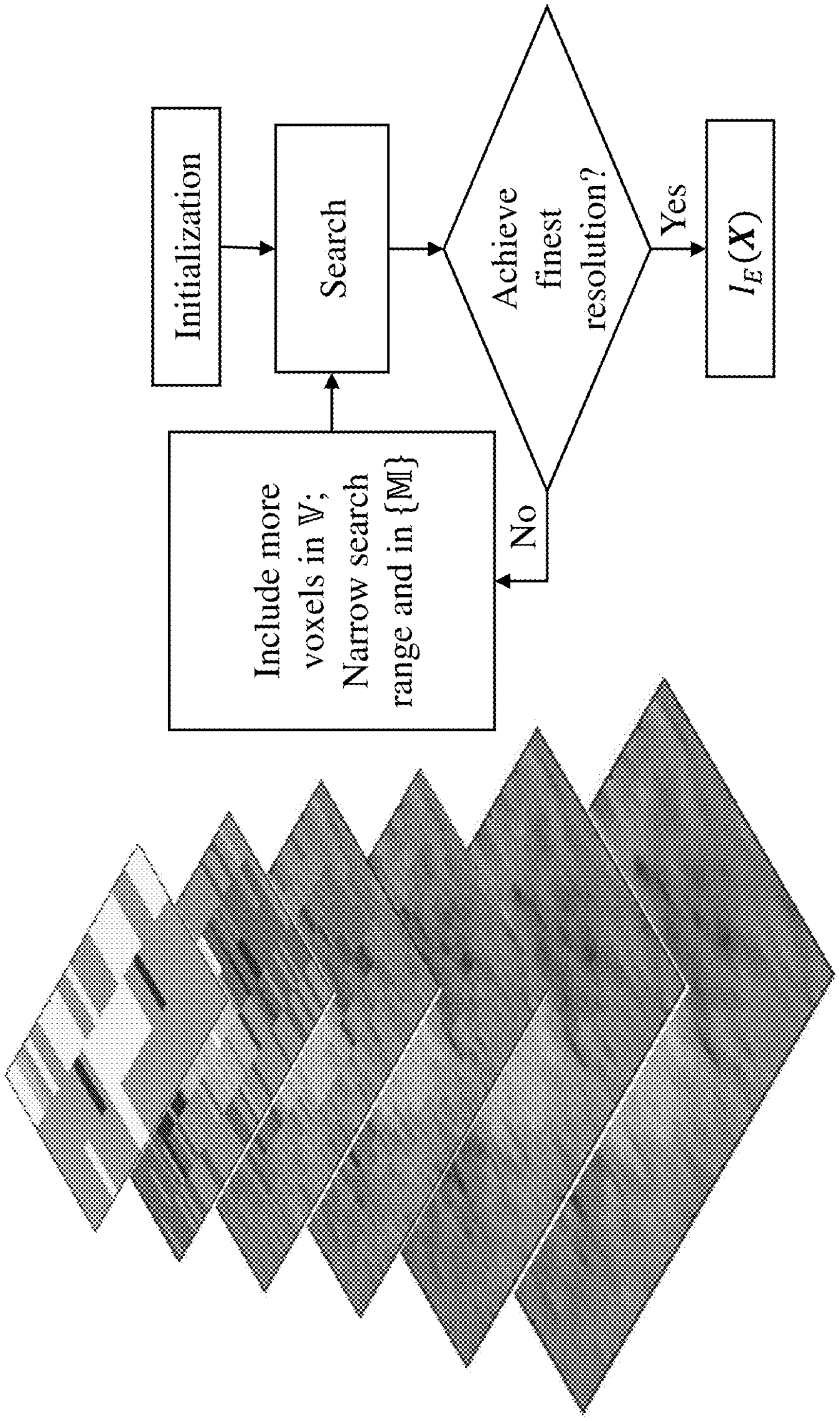
FIG. 2A (left) shows a visual illustration of a coarse-to-fine search strategy and FIG. 2A (right) shows a flowchart illustrating the coarse-to-fine search strategy of a conventional "baseline" coupled filtering method.

Specifically, the coupled filtering method combines the filtering step based on (6) with block matching to compensate for feature motion decorrelation and therefore can achieve high accuracy in large tissue deformation analysis. FIGS. 2A (right) and 2B illustrate the workflow of the coupled filtering method. Note that the motion model (5) can allow the search for T by simply sampling across the inversely mapped image rather than repeating the entire coupled filtering procedure. This concept can help save computational load, which is adopted in the "baseline method" (described in the later section).

Figure 2B:
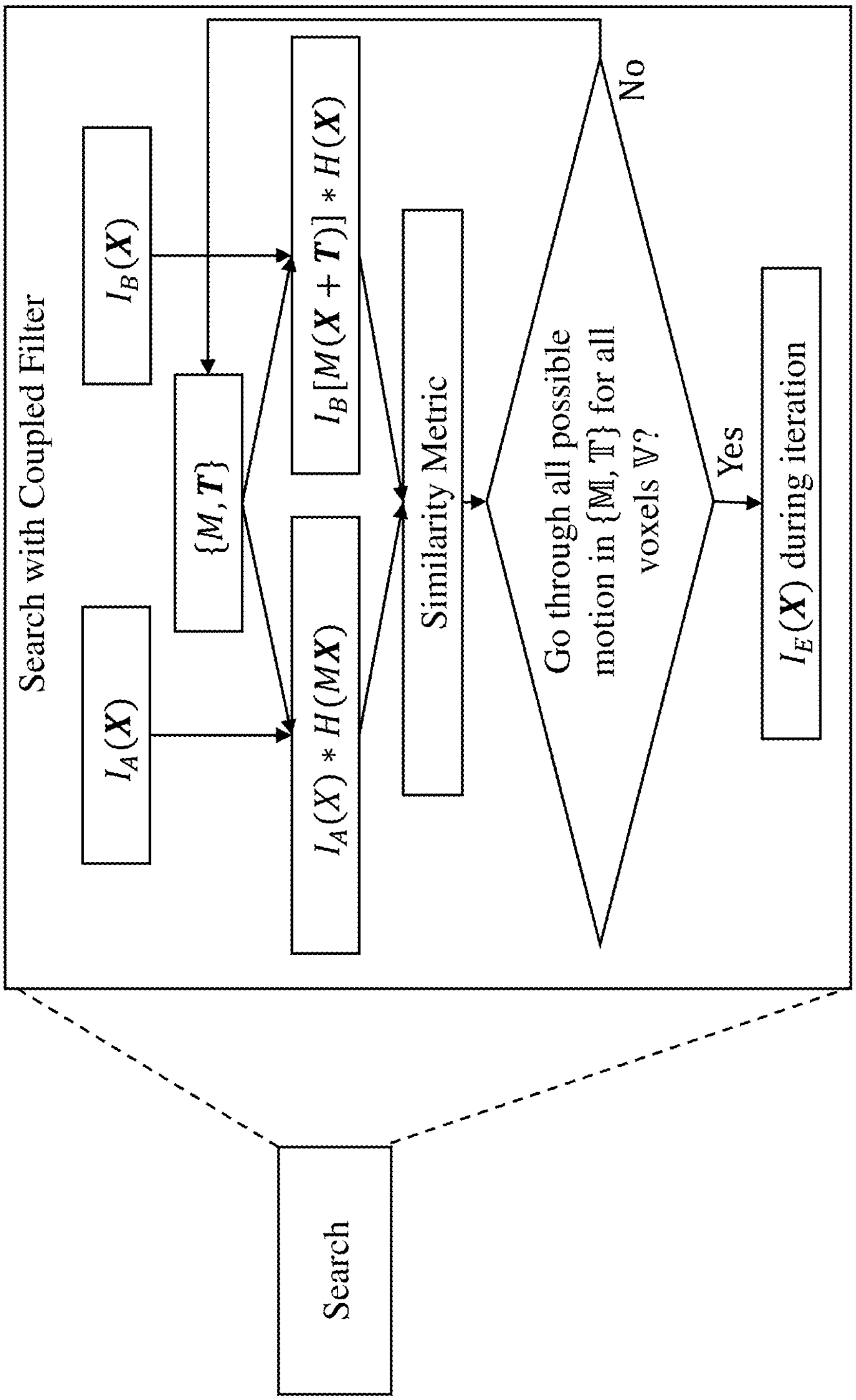
FIG. 2B shows a flowchart illustrating a detailed search process of a conventional "baseline" coupled filtering method.

Further, the coupled filtering method can adopt a coarse-to-fine search strategy to reduce the computational cost. As shown in FIG. 2A, this strategy first focuses on a small number of points and generates a rough low-resolution output, namely the first scale/iteration, and then gradually refines the result by increasing the resolution and using smaller search steps in the subsequent scales/iterations. FIG. 2B illustrates a detailed process flow of the search step. The iteration repeats until all points are processed. In the present disclosure, the coupled filtering method described above together with the coarse-to-fine search strategy adopted is referred to as the "baseline method".

FastCF

In this section, the present disclosure describes the algorithmic optimizations of FastCF. The post-processing step that helps maintain the accuracy of the estimated strain is also described.

FastCF Parameters

Firstly, three search spaces are defined as follows:

$$\mathbb{V} = \{V \in \mathbb{R}^{3\times1} | V = V_{step} \otimes J - V_{range}/2, |V| \lesssim V_{range}/2, J = [j_i \in \mathbb{Z}]_{3\times1}\}$$

$$\mathbb{M} = \{M \in \mathbb{R}^{3\times1} | M = M_{step} \otimes J + I_3 |M - I_3| \lesssim M_{range}/2, J = [j_i \in \mathbb{Z}]_{3\times3}\}$$

$$\mathbb{T} = \{T \in \mathbb{R}^{3\times1} | T = T_{step} \otimes J, |T| \lesssim T_{range}/2, J = [j_i \in \mathbb{Z}]_{3\times1}\}$$

where $V_{index} \in \mathbb{R}^{3\times n_b^3}$ denotes the coordinates of voxels in a block. $V_{range}$, $V_{step}$, $T_{range}$, $T_{step} \in \mathbb{R}^{3\times1}$ and $M_{range}$, $M_{step} \in \mathbb{R}^{3\times3}$ denote the range and step of the coordinates of points of interest, M, and T respectively; $\lesssim$ denotes the element-wise less than operator; $\otimes$ is element-wise multiplication; $\mathbb{R}^{3\times1}$ is the set of a vector sized 3-by-1; $\mathbb{R}^{3\times3}$ is the set of a vector sized 3-by-3; $\mathbb{Z}$ is the set of integers; $I_3$ is the 3×3 identity matrix.

In further details, V denotes the points of interest. Theoretically, each point in the original image is only linked to another position in the deformed image (post-deformation image). Hence, only two vectors are required to describe these two corresponding positions. Alternatively, the original position (i.e., V) and a displacement vector can also be used to describe these two corresponding positions. However, in order to determine if these two points matches, simply comparing the voxel value of these two points may not be enough because there may be other factors, such as noise or feature motion decorrelation, which may interfere with the accuracy of the result. As such, the voxel value of voxels surrounding the points of interest can be taken into consideration, i.e., matching a block of voxels in the original image (pre-deformation image) to a block of voxels in the deformed image. In this regard, a simple displacement vector may not be sufficient to account for such huge number of voxels (e.g., 200 voxels in each block). As a result, a more complex motion model, i.e., the affine transformation, X'=M (X+T), is adopted.

Next, the present disclosure describes how the search space $\mathbb{M}$ can be reduced in order to speed up the search. From Equations (1) and (6), the following Equation (7) can be obtained:

$$I_B[M(X+T) = Z(X) * H(MX)] \tag{6}$$

Comparing the pre-deformation image as described in Equation (1) and the post-deformation image as described in Equation (6), it can be seen that the key difference, among other things (if any), lies in H(X) and H(MX). Further, the point spread function H(X) as described in Equation (2) has a Gaussian shape in both x and y directions but is a Gaussian-weighted cosine function (e.g., Gabor function) in the z direction. Therefore, by comparing H(X) and H(MX), it can be observed that changes in all three directions can cause interference between two Gaussian envelopes, but only changes in the z direction would cause significant interference between the peak and trough of the Gaussian-weighted cosine function, which can lead to larger decorrelation between the pre-deformation image (as described in Equation (1)) and the post-deformation image (as described in Equation (6)) and, in turn, degrades the accuracy of estimated stiffness.

However, if it is defined that $$M_c = \begin{bmatrix} 1 & 0 & 0 \\ 0 & 1 & 0 \\ m_{zx} & m_{zy} & m_{zz} \end{bmatrix},$$

the observation can be summarized as follows:

$$H(M_c X) \approx H(MX) \tag{7}$$

$$\text{when } |m_{xx}-1| + |m_{xy}| + |m_{xz}| + |m_{yx}| + |m_{yy}-1| + |m_{yz}| \leq 0.6,$$

It may be worth reiterating that $M_c$ and $|m_{xx}-1|+|m_{xy}|+|mx_z+|m_{yx}|+|m_{yy}-1|+|m_{yz}|\leq 0.6$ are formulated under the assumption that only changes in the z direction would cause significant interference between the peak and trough of the Gaussian-weighted cosine function. In other words, changes in the motion parameters, $m_{xx}$, $m_{xy}$, $m_{xz}$, $m_{yx}$, $m_{yy}$, and $m_{yz}$, may be negligible as long as they meet the above defined conditions. Additionally, under the above defined conditions, it should be noted that $$M_c^{-1}M \approx I.$$

In further details regarding Equation (8), the following equations are first formulated based on both ends of Equation (6):

$$I_{1-ori}(X) = I_A(X) * H(MX) \tag{9}$$

$$I_{2-ori}(X) = I_B[M(X+T)] * H(X) \tag{10}$$

However, performing convolution for all possible Ms based on the above two Equations (9) and (10) can take too much time. Therefore, in order to reduce the amount of time taken to perform convolution, the following three Equations are further formulated:

$$I_1(X) = I_A(X) * H(M_c X) \tag{11}$$

$$I_{2t}(X) = I_B(X) * H\left(M_c^{-1} X\right) \tag{12}$$

$$I_2(X) = I_{2t}[M(X+T)] \tag{13}$$

Using Equations (11) and (12), $I_1(X)$ and $I_{2t}(X)$ only need to be calculated when $M_c$ changes. As $M_c$ only has 3 independent variables, i.e., $m_{zx}$, $m_{zy}$ and $m_{zz}$, calculation time can be significantly reduced as compared to calculating M, which, at the maximum, has 8 independent variables (9 in total, minus one due to the assumption of tissue incompressibility). Further, calculation of $I_2t[M(X+T)]$, i.e., Equation (13), can be performed by re-sampling the image. As a result, the time complexity of calculating Equation (13) is $$O\left[n_i^3\right],$$

whereas the time complexity of convolution is $$O\left[n_i^3 \log(n_i)\right].$$

Therefore, it is evident that adopting Equations (11) to (13) is more efficient.

Further, based on Equations (12) and (13), the following Equation (14) can be derived:

$$I_2(X) = I_{2t}[M(X+T)] = I_B[M(X+T)] * H\left(M_c^{-1} MX\right) \tag{14}$$

As described above, $$M_c^{-1}M \approx I$$

when under the defined conditions in relation with Equation (8). Therefore, the following relationship can be obtained:

$$I_2(X) = I_B[M(X+T)] * H\left(M_c^{-1}MX\right) \approx I_B[M(X+T)] * H(X) = I_{2-ori}(X) \quad (15)$$

Similarly, based on Equation (8), the following Equation (16) can be derived:

$$I_1(X) = I_A(X) * H(M_cX) \approx I_A(X) * H(MX) = I_{1-ori}(X) \quad (16)$$

$$\text{when } N \approx 10 * \frac{S}{8(2\ln 2)^{3/2}\sigma_x\sigma_y\sigma_z}$$

where S is defined as the volume of the imaging area. This condition defines that the number of scatterers used in the simulation should reach around 10 per resolution cell to form the speckle in ultrasound images.

As Equation (6) defines that $I_A(X)*H(MX)=I_B[M(X+T)]*H(X)$, then $I_1(X) \approx I_2(X)$.

In summary, based on Equations (14) to (16), the following relationship can be derived:

$$I_{2t}[M(X+T)] = I_B[M(X+T)] * H\left(M_c^{-1}MX\right) \approx I_B[M(X+T)] * H(X) \approx I_A(X) * H(M_cX) \quad (17)$$

In particular and as would be appreciated by the person skilled in the art, the approximate Equation (17) indicates that after the calculation of $I_A(X)*H(M_cX)$ and $$I_B(X) * H\left(M_c^{-1}X\right),$$

if the changes in the other six motion parameters fulfil the above defined condition, i.e., less than the threshold defined above, there is no need to recompute the convolution. Advantageously, as convolution is more time-consuming than computing $I_{2t}[M(X+T)]$, this implementation can help save time. Further, the filtering scheme in different stages of coarse-to-fine iterations can be adjusted. For example, during the last two iterations, or namely the last two scales, the filtering step would account for over 90% of the total computation load. Thus, the user may apply the filtering step only once without compromising on the accuracy of the results. Specifically, since the searching step $M_{step}$ is designed to be small in comparison with the search space in these scales, such a small shift would not degrade the result significantly.

Also, in example embodiments, three motion parameters, for example $m_{xy}$, $m_{yy}$, and $m_{zy}$, can be omitted from the motion model as described in Equation (5). This omission can be done by flattening the 3D block along the y (elevational) direction, which makes these three variables/motion parameters meaningless when calculating M(X+T). Originally, the incompressibility constraint already omits one motion parameter from the total number of motion parameters to be searched, i.e., reduced from a total of 9 motion parameters to 8 motion parameters. However, in the above example embodiments, three motion parameters are eliminated, i.e., $m_{xy}$, $m_{yy}$, and $m_{zy}$, which makes the incompressibility constraint to no longer take effect. Hence, $m_{xy}$, $m_{yy}$, and $m_{zy}$ are omitted from a total number of 9 motion parameters (instead of 8). Consequently, this implementation can advantageously accelerate the computation by reducing the total motion parameters to be searched by two motion parameters from M, i.e., from 8 motion parameters (incompressibility constraint is in effect) to 6 motion parameters. It would also be appreciated by the person skilled in the art that more motion parameters may be removed, depending on the desired accuracy. Additionally, in the above example embodiments, the axial direction (z direction) is retained because it has the highest resolution. Further, the elevational direction (y direction) is omitted/flattened because it usually has lower resolution than the lateral direction. In other words, retaining the axial and lateral directions may ensure accurate results to be obtained.

Putting it all together, Mc can be defined as the matrix used in the filtering step as follows:

$$M_c = \begin{cases} M_c = [100;\, 010;\, m_{zx} 0\, m_{zz}] & \text{, scale} = 1 \\ M_{opt}(V) & \text{, scale} \geq n_s - 1 \\ \begin{bmatrix} M_{opt,xx}(V) & 0 & M_{opt,xz}(V) \\ M_{opt,yx}(V) & 1 & M_{opt,yz}(V) \\ m_{zx} & 0 & m_{zz} \end{bmatrix} & \text{, others} \end{cases} \quad (18)$$

Algorithm 1 below presents the algorithm with the updated filtering step. The envelope function will be described in the next section. In Algorithm 1, multiple loop sequences are defined for different search scales. Specifically, with reference to FIG. 3, in the first scale/iteration (scale/iteration=1), the search range of T, i.e., $\mathbb{T}$, is relatively large, whereas the search space of M, i.e., $\mathbb{M}$, is the same for all the points of interest, so it is worth calculating on the entire image. On the other hand, the subsequent scales/iterations (scale/iteration >1) have smaller $\mathbb{T}$ and different points have different $\mathbb{M}$s, so it is suitable for calculating only part of the image.

ALGORITHM 1

Filtering Step in FastCF

```
Function [M_opt, T_opt, C_opt] = SearchCoarse(all input) // scale = 1
  For M ∈𝕄
    If M_c changes
      I_1(X) = Envelope(I_A(X) * H(M_cX))
      I_2t (X) = Envelope(I_B(X) * H(M^-1_cX))
    For V ∈𝕍
      I_2(X) = I_2t(MX)
      Search for the best T
Function [M_opt, T_opt, C_opt] = SearchFine(all input) // scale > 1
  For V ∈𝕍
    For M ∈𝕄
    M = M + M_opt (V)
    If M_c changes
      I_1(X)= I_A(X) * H(M_cX)
      I_2t(X) = I_B(X) * H(M^-1_cX)
        // Only for X in surrounding area
    I_2(X) = I_2t(MX)
    Search for the best T
```

Envelope Detection

Figure 4:
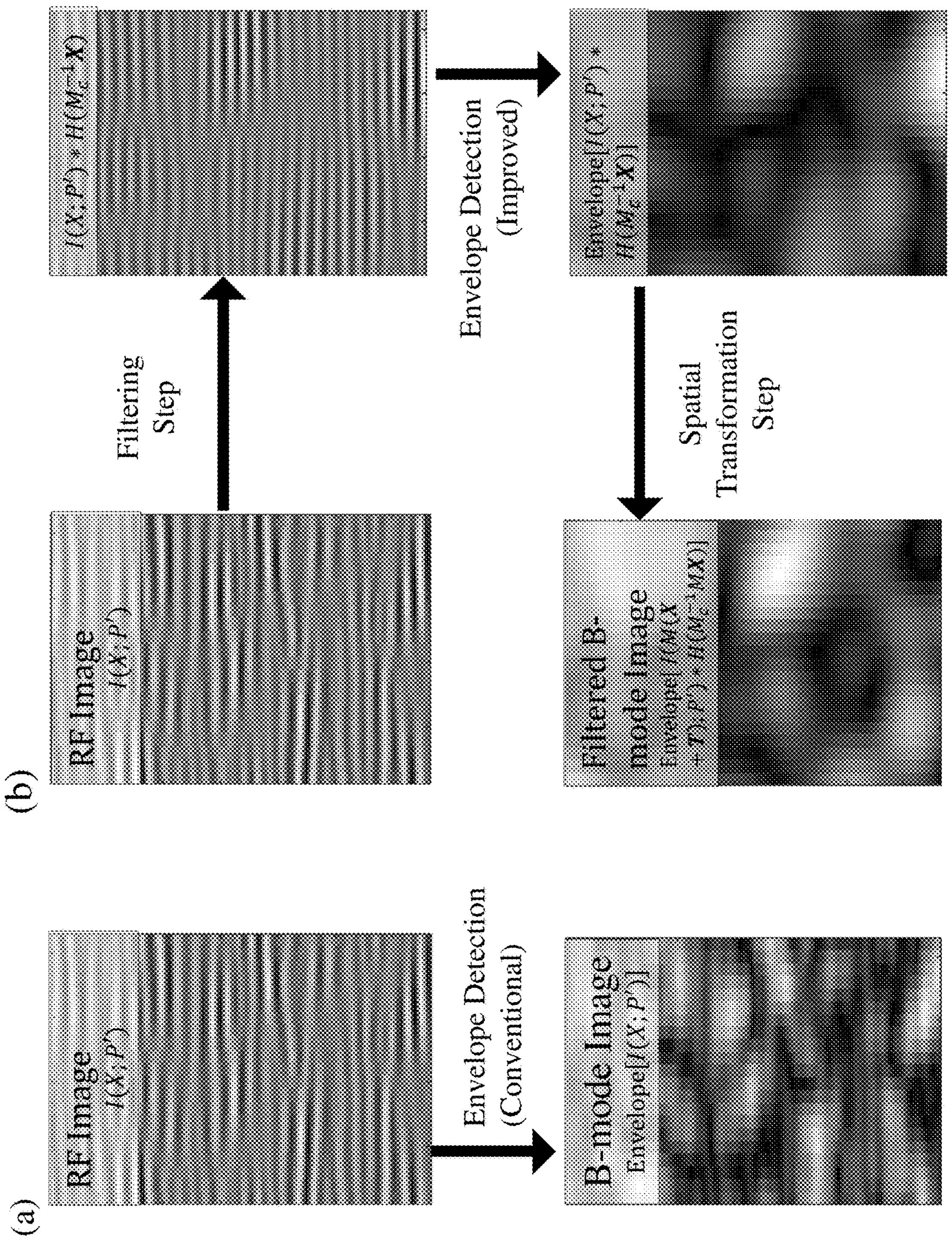
FIG. 4 shows a flowchart illustrating (a) a conventional process of converting a Radio Frequency (RF) image to B-mode image and (b) a process of a RF image to B-mode image in accordance with an embodiment.

After the filtering step as described above, the images may retain wavy shapes, and their envelopes can contain useful information for deformation analysis. Therefore, embodiments of the present disclosure provide a method to detect these envelopes and aim to take advantage of the image envelope(s) in the filtering step such that the search can proceed at much larger steps at the coarsest scale. In more details, Radio-Frequency (RF) signal is the raw signal coming out of the ultrasound sensor, and B-mode signal is easier to interpret. Embodiments of the present disclosure provide a different workflow to detect the envelope(s) of filtered RF signal and convert it into filtered B-mode signal(s), as shown in FIG. 4, which allows the search steps to be enlarged without causing severe peak hopping issue in RF signal-based motion tracking. Specifically, with reference to FIG. 4, a filtering step can be applied to an RF image, e.g., pre-deformation image or post-deformation image. Thereafter, detection of envelope(s) can be performed to the filtered RF image. Finally, a spatial transformation step can be performed to obtain a Filtered B-mode image. The order of performing the above-mentioned process steps can be changed. Advantageously, performing the spatial transformation step after filtering the RF image can improve computation speed.

Additionally, the original RF signal can have a very large spatial frequency in the axial direction, e.g. for a 3 MHz ultrasound signal and a sampling speed of 15.4 MHz, peak and trough can be found in every 5.1 voxels. This can mean that, with a slight shift in the M and T, the resulting image I(MX+T) may look different, and it can be easy to mismatch the peaks and troughs. Hence, the search steps of M and T are set to be relatively small so that the blocks can be correctly matched by combining the patterns of an entire block. With envelope detection, the spatial frequency of the wavy signal can be decreased by around 5 to 7 times as shown in FIG. 4, e.g., one peak and one trough for every 30 voxels. This means that the original search step of M and T can be increased by around 6 times, and it would still enable the correct matching of peaks and troughs while mitigating the peak hopping issue. Consequently, a rough search can be applied at the beginning and the result can be finalized with smaller search steps thereafter. Importantly, it would be appreciated by the person skilled in the art that the above conversion process can be applied together with the coarse-to-fine multi-scale strategy for further acceleration. The envelope is the L1-norm of the Hilbert transformed signal. The algorithm of the updated coarse-to-fine strategy is shown in Algorithm 2.

It may be worth mentioning that the flattening is performed on the blocks (or one or more voxels) of the images, rather than on the images. In other words, when using a similarity metric to measure the similarity between two corresponding points in pre- and post-deformation images, only a flattened region of interest is considered, i.e., blocks including X*1*Z number of voxels, in both the pre- and post-deformation images. Specifically, when calculating the similarity metric, only the voxels in the 2D blocks are considered. However, in order to accurately calculate the values of these 2D blocks, it may still be necessary to consider the voxels surrounding the voxels of these 2D blocks as the voxels in other elevational planes may affect the accuracy of the result.

ALGORITHM 2

Updated Coarse-to-Fine Strategy in FastCF

```
For scale in { 1,2, ... , n_s}
  If scale == 1
    V_step ×= 2^(n_s −1)
    M_step ×= 2^(n_s −1);T_step = [2 2 2]^T
    SearchCoarse( )
  Else
    V_step /= 2; M_range /= 2; T_range /= 2
    M_step /=2;T_step = [1 1 1]^T
    SearchFine( )
```

Post-Processing

Peak hopping is common in RF image-based tissue deformation analysis, and it can degrade the motion tracking results. To address this issue, embodiments of the present disclosure provide a post-processing step based on majority voting. Particularly, it is observed that the axial displacement, i.e., $D_z$, is more accurate than the other two directions. Consequently, based on this observation, limits can be imposed on the gradients of $D_z$ in three directions. For example, by defining two adjacent points P, Q $\in \mathbb{V}$ with $P-Q=[V_{step,x}\ 0\ 0]^T$, and the displacement $D_{opt}(V)=M_{opt}(V)(V+T_{opt}(V))-V$, with the Lagrangian motion model, the following limits can be derived:

$$m_{zx,min} \leq \frac{D_{opt,z}(P) - D_{opt,z}(Q)}{V_{step,x}} \leq m_{zx,max} \tag{19}$$

where $[m_{zx,\ min}, m_{zx,\ max}]$ is the search range of $m_{zx}$.

Figure 5:
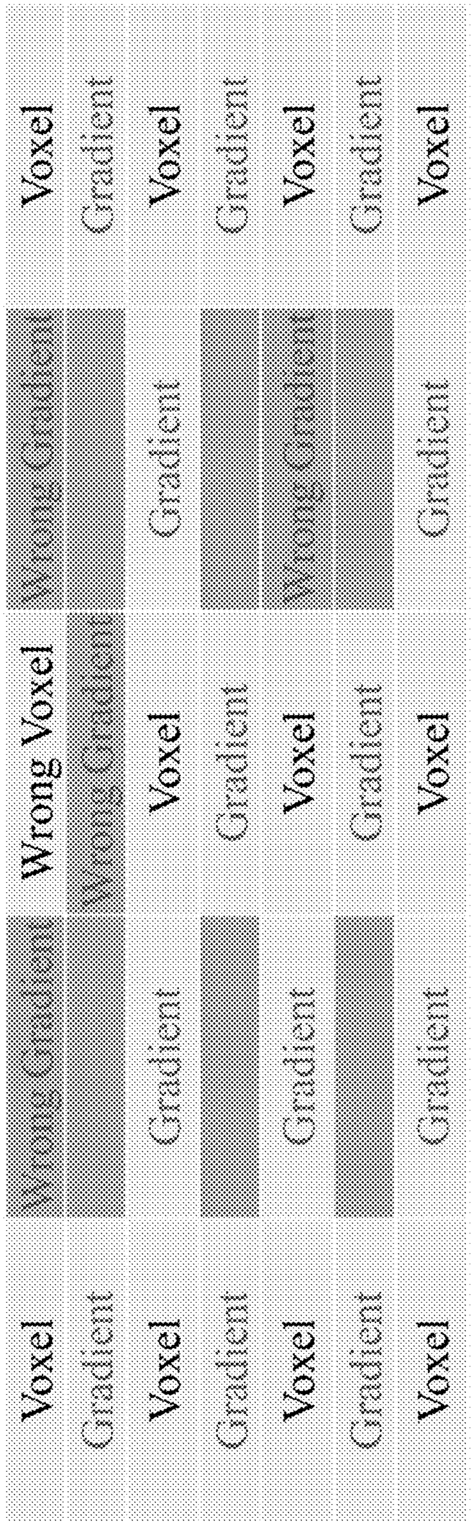
FIG. 5 shows an example scenario of a post-processing step, in accordance with an embodiment.

Similar limits can also be established along the other two directions. With reference to FIG. 5, any gradient exceeding these theoretical limits can be recognized to be wrong, and the voxels surrounded by wrong gradients can be defined as wrong voxels. Subsequently, the M and T of the wrong voxels can be interpolated based on the correct voxels and let the finer scales refine the results. Usually less than 5% are wrong voxels, and other voxels are not affected. Also, the post-processing step can be designed to be light-weight and does not substantially slow down the overall computing time. The results of the post-processing step are discussed in the later section of this disclosure. The post-processing step algorithm is shown in Algorithm 3 below.

ALGORITHM 3

Post Processing in FastCF

```
Function [M_opt, T_opt, D_opt] = PostProcessing(D_opt)
  Initialize a graph with vertices representing 𝕍 and edges connecting all adjacent vertices
  while(not all vertices are marked or a new wrong area is found)
    Delete the edges that exceed a limit
    Find the largest connected component and mark it correct
    Find the connected component(s) adjacent to the correct connected component and mark it/them
wrong
    Interpolate D_opt for the wrong area and mark them correct
  Interpolate M_opt, T_opt for all vertices
```

FastCF Algorithm

The overall algorithm of FastCF is presented in Algorithm 4 and described in this section. When searching for the optimal T in Algorithm 1, the sum-tables method can be adopted. In example embodiments, the CPU implementation is coded in MATLAB. In the first scale/iteration, the computation is parallelized after calculating $I_1(X)$ and $I_2temp(X)$; in the remaining scales/iterations, the computation of all Vs is parallelized. Further, the MATLAB code for the interpolation and searching for the best T with the C++ MEX functions is also re-implemented. Pointer and dimension permutation are also adopted. In the post-processing step, the graph can be stored in the form of 3D matrix, of which elements with odd coordinates represent the vertices as shown in FIG. 5. Each vertex represents one voxel in $\mathbb{V}$, and can be connected to its adjacent vertices only when the difference of their $D_{opt}$ falls into the theoretical limit. The MATLAB built-in function bwlabeln( ) is then utilized, which helps find connected components in binary image, to accomplish the relevant graph operations.

ALGORITHM 4

FastCF

Figure 6:
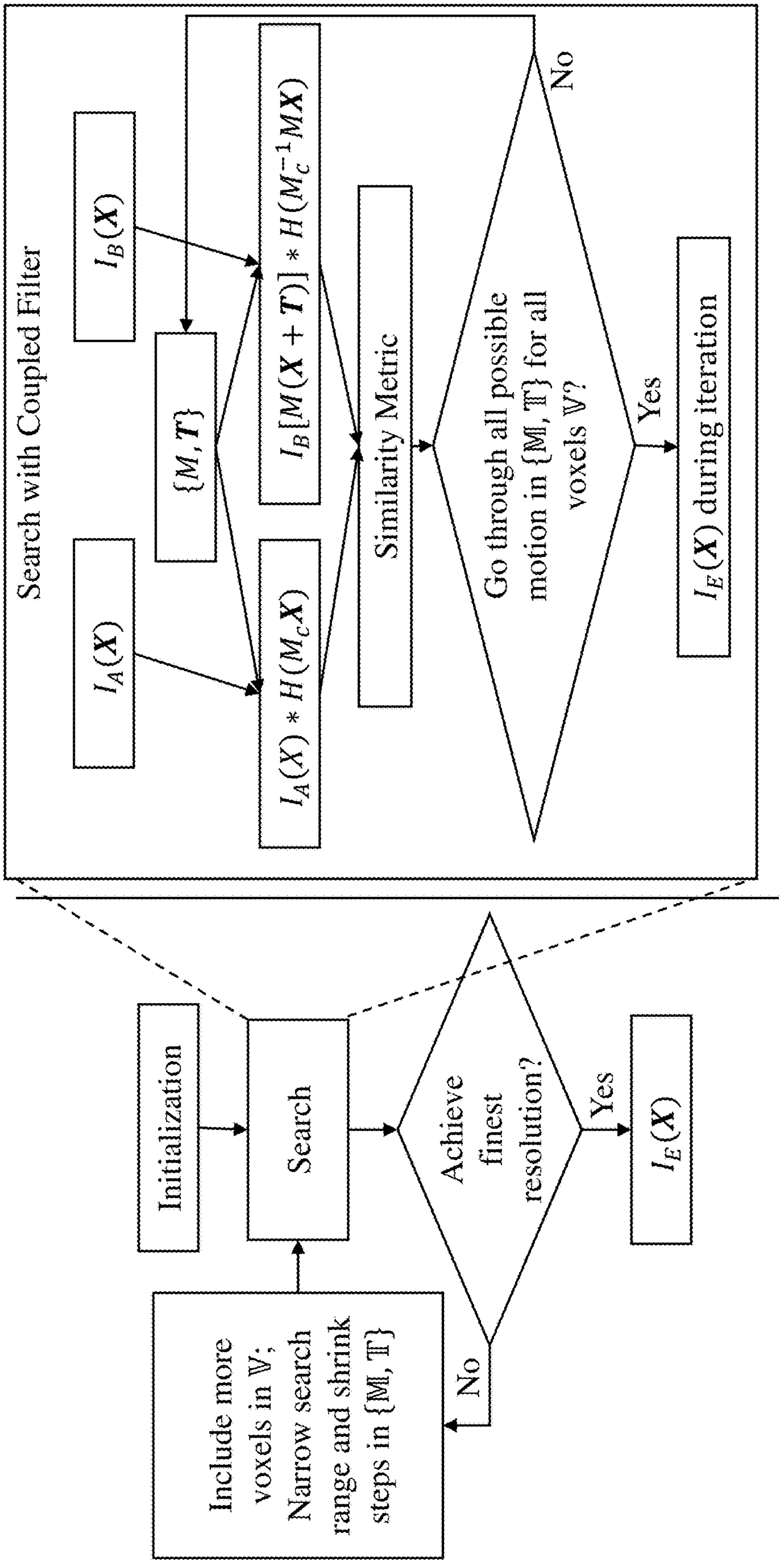
FIG. 6 shows a flowchart illustrating an overview of an accelerated coupled filtering method ("FastCF"), in accordance with an embodiment.
Figure 7:
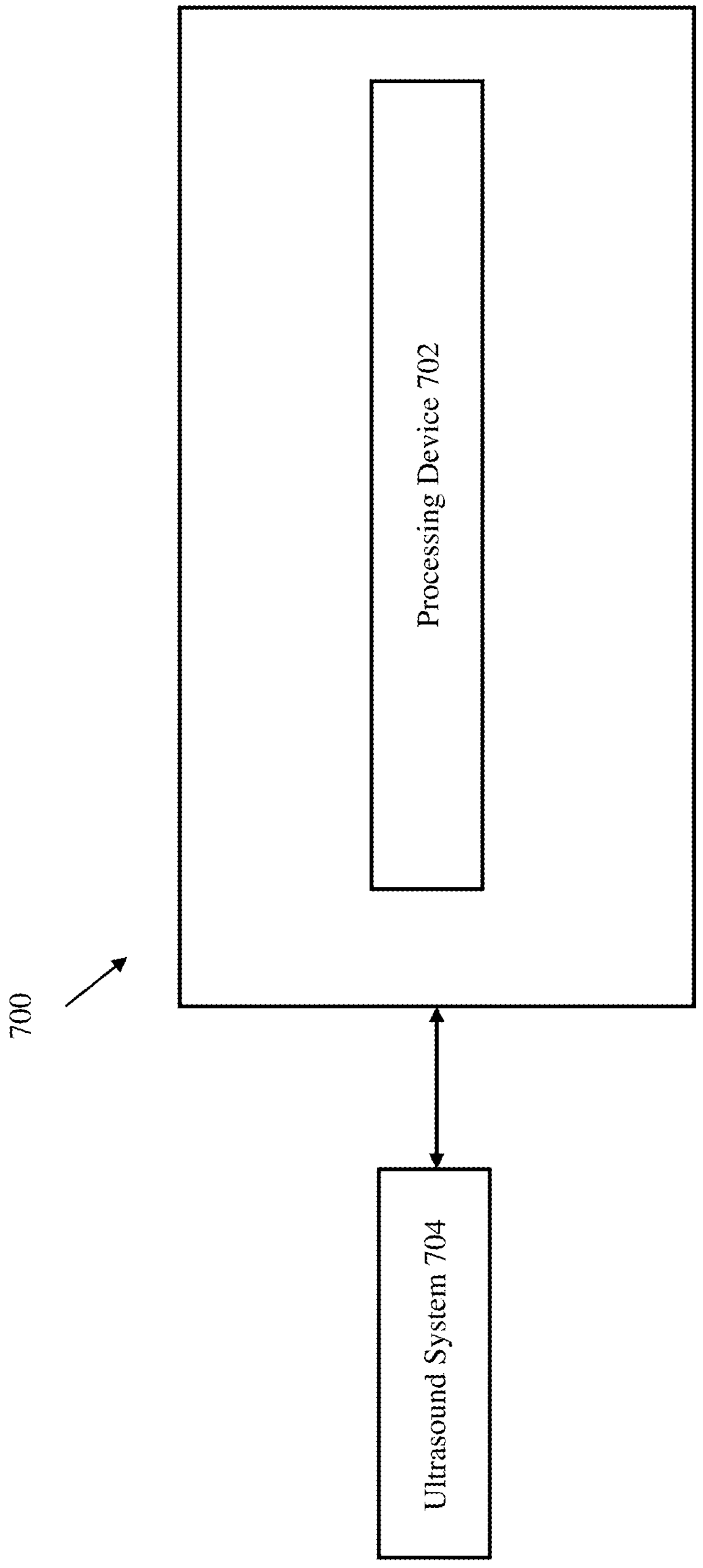
FIG. 7 shows a schematic diagram of an exemplary system for performing an accelerated coupled filtering method for tissue deformation analysis, in accordance with an embodiment.

Input:
1) Image $I_A = I(X; P) \in \mathbb{R}^{n_i^3}$ and $I_B = I(X; P') \in \mathbb{R}^{n_i^3}$
2) $m_{zzMax}$: expected maximum axial strain
3) $\sigma_x$, $\sigma_y$, $\sigma_z$, $u_z$, H (X) parameters derived from imaging parameters
Output:
An image $I_E \in \mathbb{R}^{n_i^3}$ depicting estimated axial strain $m_{zz}$
Algorithm:
Initialization
For scale in $\{1,2, \ldots, n_s\}$
  Search with the updated coarse-to-fine strategy
  If scale <= 4
    PostProcessing( )
Summarize the result and generate the output image FIG. 6 provide an overview of an exemplary process flow of the method, i.e., "FastCF", described in the present disclosure. In other words, embodiments described in the present disclosure provide an accelerated coupled filtering method for tissue deformation analysis. The method can be implemented with system 700 shown in FIG. 7, which shows a schematic diagram of the system 700 for performing the accelerated coupled filtering method for tissue deformation analysis. The system 700 can include a processing device 702. In embodiments of the present disclosure, the system 700 may be communicatively coupled to an ultrasound system 704 to receive and send information/data, e.g., ultrasound images, etc. However, the person skilled in the art would appreciate that the system 700 can be communicatively coupled to other suitable system or device for performing the method, depending on the application.

Figure 8:
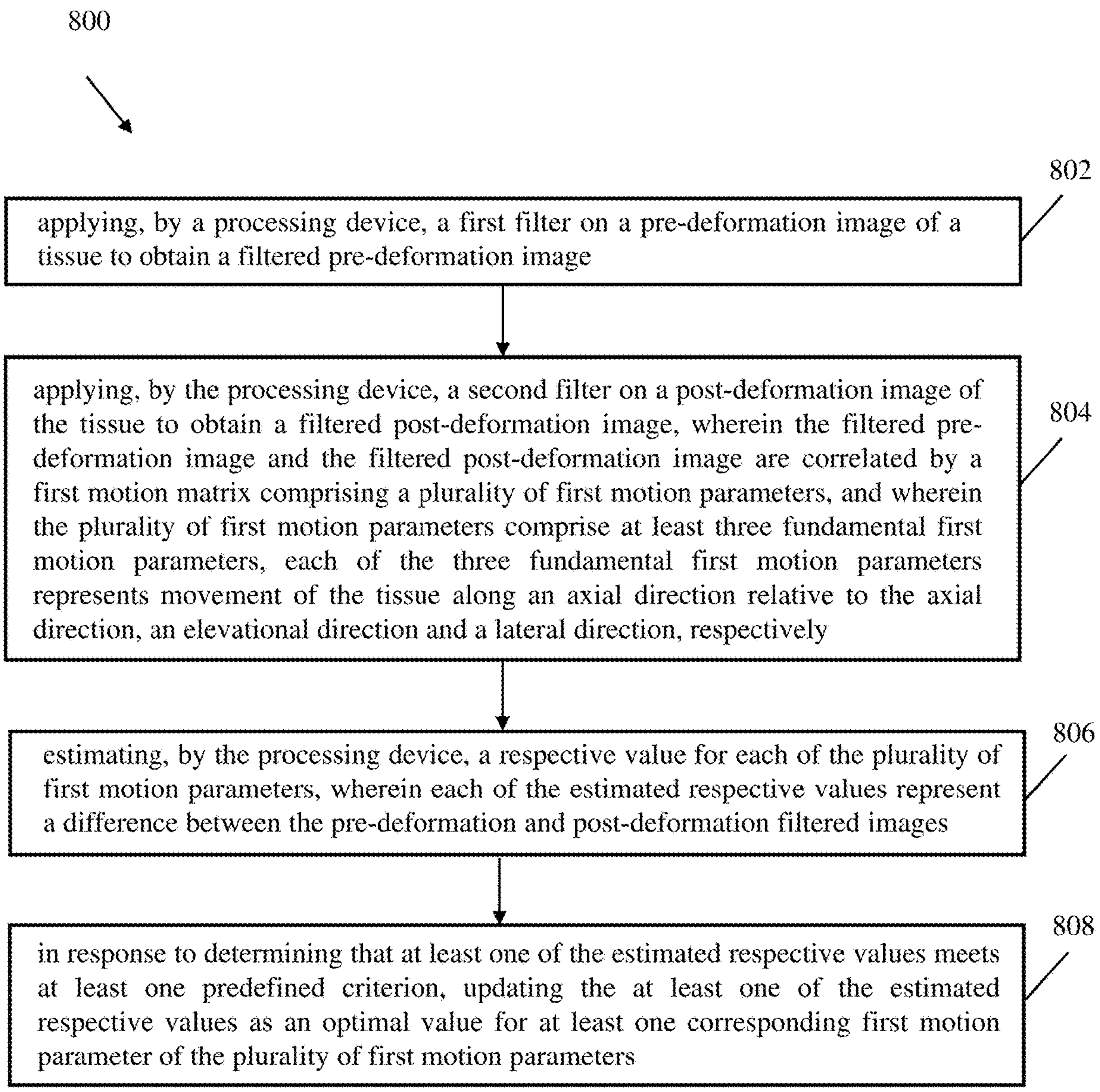
FIG. 8 shows a flowchart illustrating an exemplary workflow of an accelerated coupled filtering method for tissue deformation analysis, in accordance with an embodiment.

With reference to FIG. 8, the method 800 can include the following steps:

Step 802: applying, by a processing device, a first filter on a pre-deformation image of a tissue to obtain a filtered pre-deformation image.

Step 804: applying, by the processing device, a second filter on a post-deformation image of the tissue to obtain a filtered post-deformation image.

The filtered pre-deformation image and the filtered post-deformation image are correlated by a first motion matrix including a plurality of first motion parameters. The plurality of first motion parameters include at least three fundamental first motion parameters. Each of the three fundamental first motion parameters represents movement of the tissue along an axial direction relative to the axial direction, an elevational direction and a lateral direction, respectively.

Step 806: estimating, by the processing device, a respective value for each of the plurality of first motion parameters. Each of the estimated respective values represents a difference between the pre-deformation and post-deformation filtered images.

Step 808: in response to determining that at least one of the estimated respective values meets at least one predefined criterion, updating the at least one of the estimated respective values as an optimal value for at least one corresponding first motion parameter of the plurality of first motion parameters. It would be appreciated by the person skilled in the art that, based on the term "corresponding", it is defined, by way of example, that if the estimated respective value of only the fundamental motion parameter representing movement of the tissue along the axial direction relative to the lateral direction meets the at least one predefined criterion, the respective value of only such fundamental motion parameter will be updated. The remaining fundamental motion parameters will not be updated.

In embodiments of the present disclosure, the method 800 can include a step of detecting, by the processing device, one or more envelopes present in the filtered pre-deformation image and filtered post-deformation image to obtain a filtered B-mode pre-deformation image and a filtered B-mode post-deformation image.

In embodiments of the present disclosure, the applying steps 802 and 804 can include convolving a first point spread function and second point spread function of an ultrasound system with the pre-deformation image and the post-deformation image, respectively. The first point spread function can be a modified version of the second point spread function.

Additionally, after applying step 804, the method 800 can include a step of spatially transforming, by the processing device, the post-deformation image based at least on a second motion matrix. The first motion matrix can be a modified version of the second motion matrix.

In embodiments of the present disclosure, the filtered pre-deformation image and filtered post-deformation image can be 3-dimensional (3D) images. The person skilled in the art would be able to appreciate that the pre-deformation, post-deformation, filtered pre-deformation and filtered post-deformation images are not solely limited to being 3D images and can encompass other image format such as 2-dimensional images, etc., depending on a user's preference and/or the application. Further, estimating the respective value can include the following sub-step.

Sub-step A: flattening, by the processing device, a first and second plurality of voxels surrounding each of one or more pre-deformation points of interest in the filtered pre-deformation image and each of one or more post-deformation points of interest in the filtered post-deformation image, respectively. The flattening can be performed along the elevational direction of each of the first and second plurality of voxels, which can reduce the plurality of first and second motion parameters.

In embodiments of the present disclosure, the estimating step 806 can be performed in a plurality of iterations. In a first iteration of the plurality of iterations, the plurality of first motion parameters can include two of the three fundamental first motion parameters representing movement of the tissue along the axial direction relative to the axial direction and the lateral direction, respectively, and the remaining fundamental first motion parameter may be removed by the flattening. Between a second iteration to a final iteration of the plurality of iterations, the plurality of first motion parameters can include the two of the three fundamental first motion parameters, two lateral first motion parameters representing movement of the tissue along the lateral direction relative to the lateral direction and the axial direction, respectively, and two elevational first motion parameters representing movement of the tissue along the elevational direction relative to the lateral direction and the axial direction, respectively.

In embodiments of the present disclosure, the second motion matrix can include a plurality of second motion parameters and the estimating step 806 can further include the following sub-steps.

Sub-step B: searching, by the processing device, a value of each of the plurality of first motion parameters for each of the one or more pre-deformation points of interest in the filtered pre-deformation image.

Sub-step C: searching, by the processing device, a value of each of the plurality of second motion parameters for each of the one or more post-deformation points of interest in the filtered post-deformation image.

Sub-step D: generating, by the processing device, one or more pre-deformation voxels based on the searched value of each of the plurality of first motion parameters.

Sub-step E: generating, by the processing device, one or more post-deformation voxels based on the searched value of each of the plurality of second motion parameters.

Sub-step F: calculating, by the processing device, a similarity metric based on one or more first voxels surrounding the one or more pre-deformation voxels and one or more second voxels surrounding the one or more post-deformation voxels. The similarity metric can define a similarity between a target pre-deformation point of interest and a post-deformation point of interest corresponding to the target pre-deformation point of interest.

Sub-step G: determining, by the processing device, if the target pre-deformation point of interest matches the corresponding post-deformation point of interest based on the calculated similarity metric.

Additionally, in embodiments of the present disclosure, the plurality of second motion parameters can include at least two fundamental second motion parameters, two lateral second motion parameters and two elevational motion parameters. The estimating step 806 can further include, in the first iteration, determining, by the processing device, a value of each of the two of the three fundamental first motion parameters based on steps (A) to (G). Between the second iteration to a third final iteration, determining, by the processing device, an updated value of each of the two of the three fundamental first motion parameters based on steps (A) to (G), and assigning, by the processing device, a value of each of the two lateral second motion parameters and the two elevational second motion parameters searched in step (C) in a previous iteration as a respective value of each of the two lateral first motion parameters and the two elevational first motion parameters. In a final two iterations, assigning, by the processing device, the determined updated value of each of the two of the three fundamental first motion parameters in the third final iteration as an optimal value of each of the two of the three fundamental first motion parameters, and assigning, by the processing device, an updated value of each of the two lateral second motion parameters and the two elevational second motion parameters searched in step (C) in the third final iteration as an optimal value of each of the two lateral first motion parameters and the two elevational first motion parameters.

In embodiments of the present disclosure, the similarity metric may include any one of the following: Normalized Correlation Coefficient, Sum of Absolute Differences and Sum of Squared Differences. However, the person skilled in the art would readily appreciate that other suitable metrics may be used, depending on a user's preference and/or application.

Furthermore, the method 800 can include the following steps: imposing, by the processing device, an upper limit and a lower limit on a gradient of a displacement range of the fundamental first motion parameters along the axial direction. Values falling outside the displacement range can be determined to be a wrong value of the fundamental first motion parameters. In response to determining that one or more voxels include the wrong value of the fundamental first motion parameters, determining, by the processing device, a corrected value of the fundamental first motion parameters of the one or more voxels. The corrected value can be determined by interpolating the wrong value based on a predetermined correct value of the fundamental first motion parameters of voxels surrounding the one or more voxels.

Evaluation

Experimental Setup

In this section, the time performance and tracking accuracy of FastCF are evaluated. The experimental setup includes hardware, software, two simulated and one real dataset, a set of parameters, and an evaluation metric. The CPU platform is AMD Ryzen Threadripper PRO 3995WX (64 cores) with 512 GB memory. The CPU program utilizes less than 64 GB of memory with 64 MATLAB workers. The CPU code was implemented and tested in MATLAB R2021b on Windows server 2022.

Dataset

Figure 9:
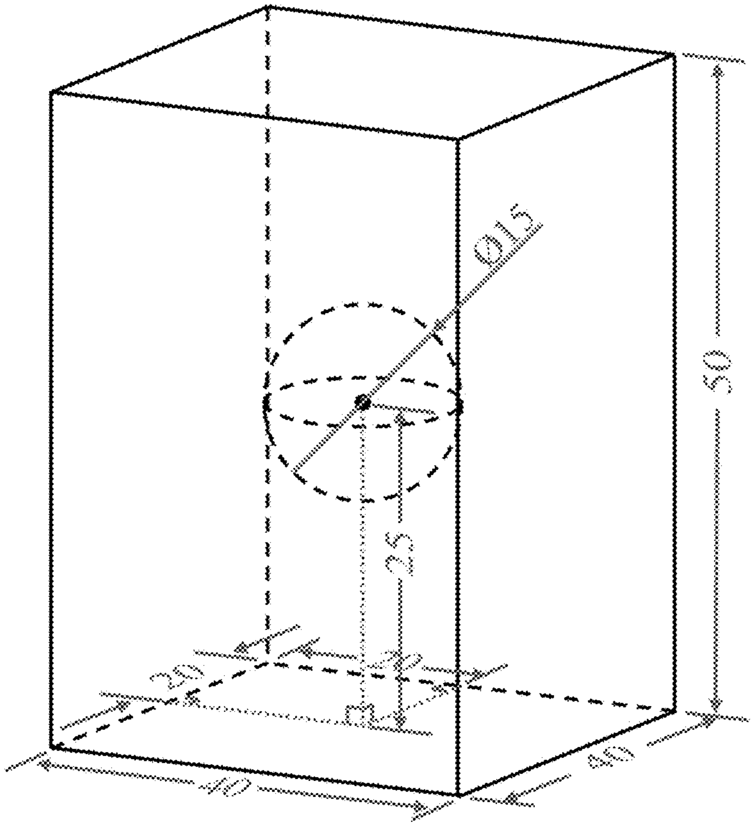
FIG. 9 shows an exemplary model of an elastic tissue, in accordance with an embodiment.

To simulate a dataset with known ground truth, SolidWorks is used to model an elastic tissue. As shown in FIG. 9, the elastic tissue has a hard spherical area merged in a soft cuboid material. The model is then uniformly compressed by 5% in the axial direction and SolidWorks is sued to simulate the movement under compression. Further, one pair of 3D ultrasound images is generated using simulation software Field II based on the simulation result and estimate the parameters of the point spread function H(X). The RF format ultrasound image is stored, and the image size is 101×101×1001 voxels. Additionally, a real 3D dataset is collected with the Philips iE33 xMATRIX ultrasound system. A X3-1 transducer is adopted to acquire 3D B-mode images of a participant's left ventricle, and the image size is 302×158×302 voxels. Two volumes are then manually selected during the contraction for illustration. Due to lack of access to the RF signal, an approximate version of the coupled filtering method is adopted by removing the filtering step as follows:

$$I_A(X) \approx I_B[M(X+T)] \tag{20}$$

Further, FastCF is also tested using 2D simulation dataset and the results are used for comparison with the baseline method.

Parameter Setting

The parameters and values of the simulated 3D dataset are defined in FIG. 10. Further, FIG. 10 also shows the time complexity, space complexity and estimated Floating Points per Seconds (FLOPs) of the 2D and 3D datasets. In FIG. 10, (a) represents coupled filtering with exhaustive search, (b) represents coarse-to-fine search strategy, (c) represents approximation of matrix M, (d) represents envelope detection, and (e) represents sum table. The other parameters are shown in FIG. 3. Additionally, FIG. 11 shows the parameters used for the time complexity and space complexity analysis for the 2D and 3D implementations of the various coupled filtering methods. In the experiment, the search range of $m_{xx}$ and $m_{zz}$ is between −10% and 10%, and the search range of $m_{xz}$, $m_{yx}$, $m_{yz}$, $m_{zx}$ is between −5% and 5%. These search ranges are sufficiently large for the dataset.

Evaluation Metrics

In the experiment, the square root of the mean square error (SRMSE) of the axial strain is used to measure the accuracy of estimation result:

$$SRMSE = \sqrt{\frac{\sum_B (\epsilon(B) - \epsilon_0(B))^2}{N_B}} \tag{21}$$

where $\epsilon(W)=m_{zz}-1$ is the estimated axial strain for a certain block B, $\epsilon_0$ (B) denotes the corresponding ground truth, and $N_B$ is the number of blocks.

In the MATLAB program, a timer "tic toc" is used to measure the running time and "mpiprofile" is used to measure the running time of different functions. Only the time initializing the MATLAB parallel pool is excluded.

FLOPs Estimation and Complexity Analysis

FIG. 12 shows the detailed time complexity of all related methods. The present disclosure also demonstrates how the time complexity and FLOPs of the exhaustive search are calculated as an example.

For the filtering step, kernels sized $$n_p^3$$

are convolved with images sized $$n_i^3,$$

which can be accelerated by the circular convolution property of the Fourier Transform. Specifically, Fast Fourier Transformation (FFT) is applied on the padded image and the result is multiplied with the transformed kernel, then inverse FFT is applied and the final result is obtained, i.e., 4 forward FFT and 2 inverse FFT to get two convolution results $I_A(X)*H(MX)$ and $I_B$ $[M(X+T)]*H(X)$. As I (X) and H(X) remain constant, they only need 2 forward FFT for the entire program. Meanwhile, 1D FFT on data sized 1×n takes $5n\log_2 n$ times operations. 3D FFT shares similar definitions except three nested summations, and each summation has the same complexity as 1D FFT, thus 3D FFT takes $15n^3 \log_2 n^3$ operations. Inverse FFT also has the same operations as FFT, and multiplication takes $n^3$ operations. Thus, the total FLOPs of the filtering step are $$(2+4n_m^8)\left[15(n_i+n_p)^3\log(n_i+n_p)^3+2(n_i+n_p)^3\right],$$

and the time complexity is $$O\left[n_i^3 \log n_i n_m^8\right].$$

Further, block-matching algorithm is adopted to search for the best results. For the interpolation step, interpolation is only performed on image for each M, and T can be achieved by sliding the window in the interpolated image. This implementation shows 30 operations for each voxel, so the FLOPs in total are $$30n_i^3 n_m^8,$$

and time complexity is $$O\left[n_i^3 n_m^8\right].$$

As for metric calculation, for $$n_o^3$$

voxels in the output, search is performed through $$n_m^8\ Ms$$

and $$n_t^3\ Ts$$

for its surrounding block sized $$n_b^3,$$

and 3 additions and 3 multiplications are performed on each voxel. Each metric also has few operations but is negligible compared to others. Therefore, the rough FLOPs of block matching are $$6n_m^8 n_t^3 n_o^3 n_b^3,$$

and the time complexity is $$O\left[n_m^8 n_t^3 n_o^3 n_b^3\right].$$

In all, the total time complexity is $$O[n_i^6 n_b^3 n_m^8].$$

Further, by adopting the approximation of M (as described above) and with reference to FIG. 12, the convolution can be reduced from $$n_m^8$$

times to $$n_m^2.$$

and the time to calculate the affine motion $I_{2r}[M(X+T)]$ can be reduced from $$n_m^8 \text{ to } n_m^6.$$

Consequently, the time complexity can drop to $$O[n_i^3 n_b^3 n_m^6].$$

If the $n_a$ blocks are simultaneously processed, the space complexity can become $$O[n_i^3 n_a].$$

Furthermore, if envelope detection is applied, approximation of matrix M can reduce the number of times to calculate the affine motion from $$n_m^6$$

to a constant, so the main computation load shifts back to convolution and the time complexity drops to $$O[n_i^3 n_b^3 \log(n_b)].$$

Results on 3D Simulated Dataset

Figure 14:
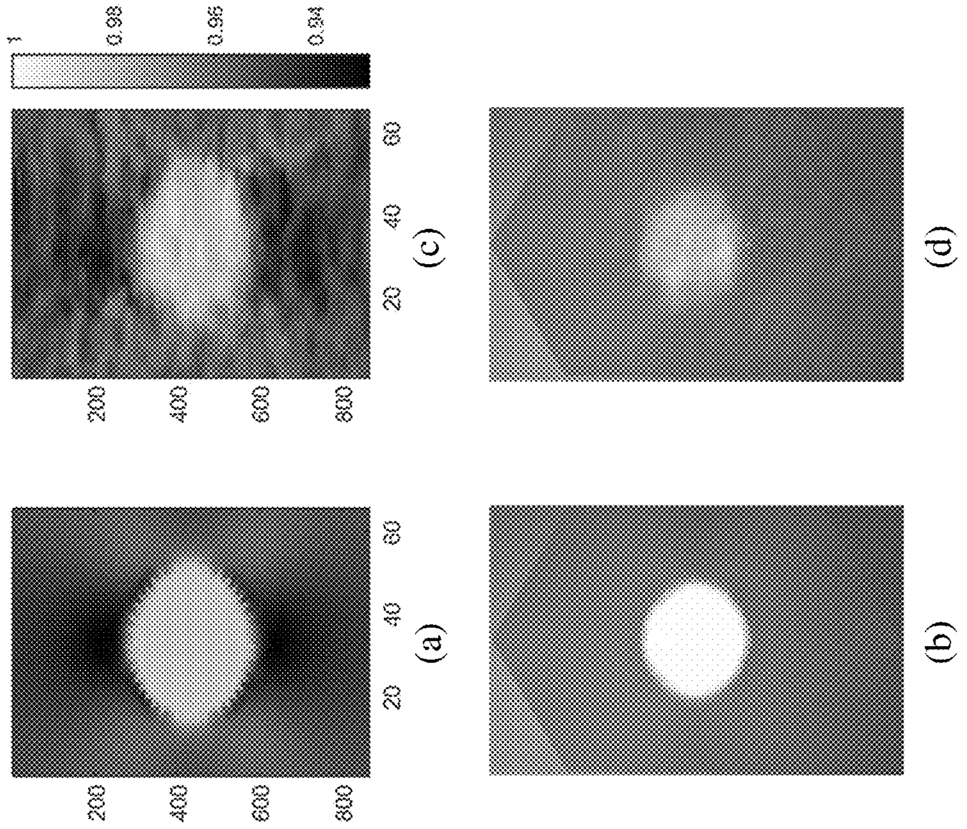
FIG. 14 shows color maps (in grayscale) illustrating results obtained from performing FastCF on the 3D simulated dataset, in accordance with an embodiment.

On the simulated 3D dataset, the estimated FLOPs and complexities of different methods are shown in FIG. 10. Both methods of M approximation and envelope detection effectively reduce the load and the usage of the sum table method also helps. In all, FastCF is estimated to reduce the FLOPs by 4.21 billion times compared to the baseline method. The mean SRMSE and the computing time at each scale are shown in FIG. 13. The results are shown in FIG. 14. As shown in FIG. 13, the SRMSE constantly decreases as the search steps of M and T get smaller. Further, with reference to FIG. 14, the final result clearly shows the hard sphere in the section view (FIGS. 14(*a*) and 14(*c*)), fulfilling the goal of tissue deformation analysis. When taking a close look at the running time of different scales, it is observed that, except for the first scale (which initializes the search), each of the other scales exhibit an increase of the number of blocks by around eight times. As such, the gradual decrease of the search space is not enough to compensate for the significant increase of number of blocks, which led to the overall computation time increasing. Additionally, as described above, the filtering strategy at the fifth scale is adjusted. As such, the fifth scale takes shorter time than others. The total time is slightly longer than the summation of all six scales' time because the interpolation between scales takes a few seconds.

Further, the computation time of different functions is analyzed, as shown in FIG. 15. In this analysis, the program is split into four main components, and the first two main components are further broken down. As shown in FIG. 15, the coupled filtering component is the most time-consuming, where the Fourier Transform relies on built-in libraries and cannot be externally optimized. Data preparation and frequency domain multiplication are likely limited by the memory speed. Further, the post-processing component takes a negligible amount of time as compared to the search process. The long computation time of other functions in the CPU implementation is mostly spent by MATLAB indexing.

Results on 3D Real Dataset

Figure 16:
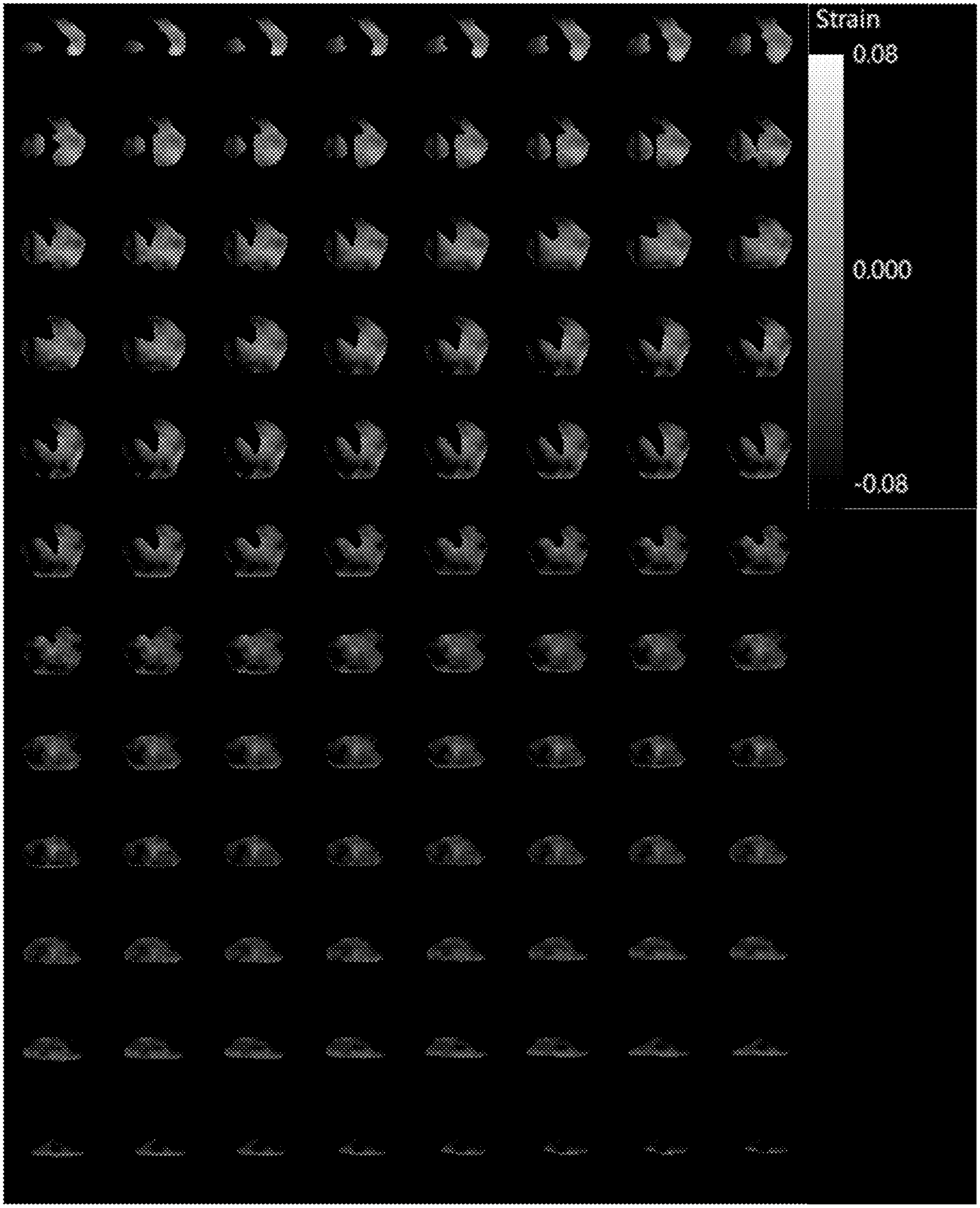
FIG. 16 shows color maps (in grayscale) illustrating results obtained from performing FastCF on 3D real data set, in accordance with an embodiment.

For the real 3D dataset, the white area near the ventricle wall is manually segmented in advance. The result is shown in FIG. 16. The analysis takes FastCF around 295 seconds to generate a strain image sized 97×65×129 on the CPU. With reference to FIG. 16, the overall compression trend in the slices is clearly visible, and further interpretation of these results would require clinical information. This dataset was generated with a frame rate of only 8 Hz. In other words, embodiments of the present disclosure can generate decent results with the ultrasound images sampled at a lower framerate, e.g., 8 Hz. In contrast, traditional deformation analysis methods require a frame rate of at least 40 Hz to 80 Hz to generate decent results.

Comparison with Baseline Method

Figure 17:
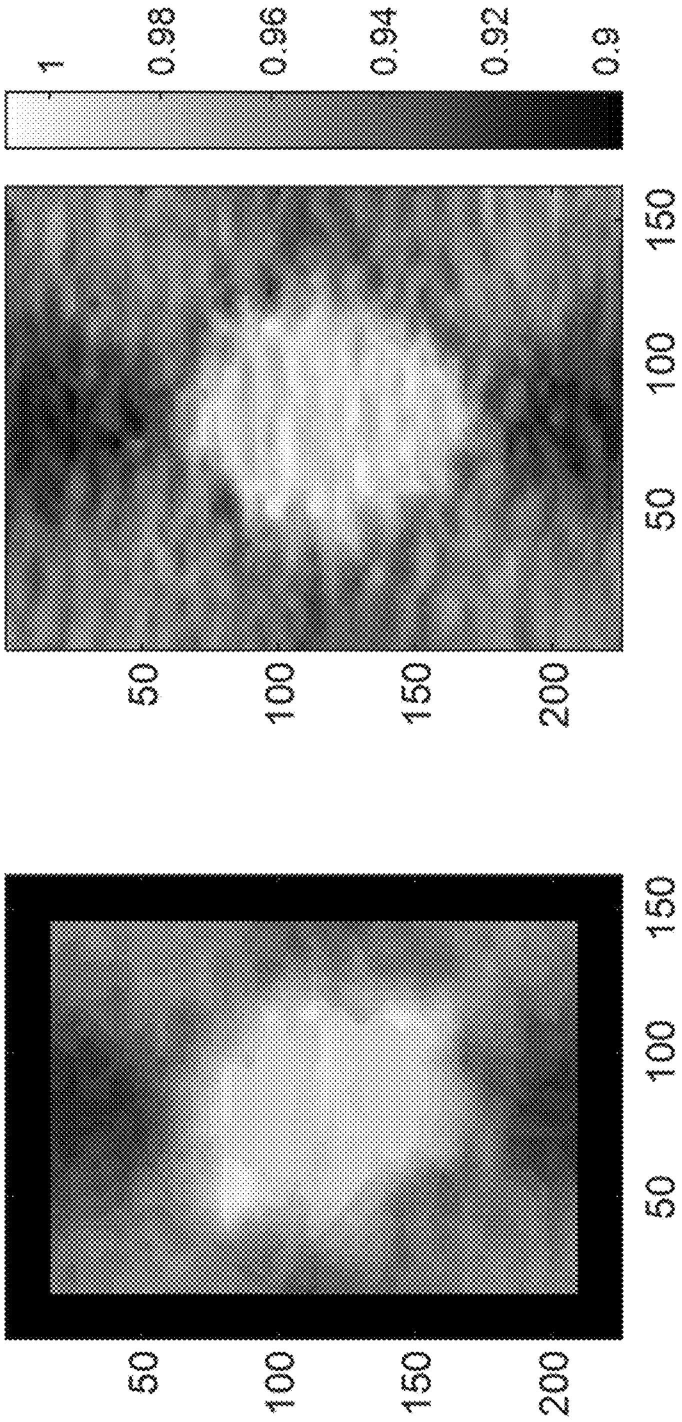
FIG. 17 shows a color map (in grayscale) of (a) baseline method and (b) FastCF performed on 2D simulated dataset, in accordance with an embodiment.

For comparison purposes, FastCF and the baseline method are performed on 2D simulated data that contains a hard cylinder. This is because performing the baseline method on 3D data will take too much time. The ground truth is similar to FIG. 14(*a*). As shown in FIG. 17, the baseline method and FastCF can both identify the hard inclusions in the 2D dataset. Further, FastCF achieves an SRMSE of 1.11% whereas the baseline achieves an SRMSE of 1.40%. FastCF also finishes the analysis within around 12.9 seconds on the CPU, but the baseline method takes around 1.72 days on the same CPU and 20 minutes on FPGA.

Verification of the Approximation of Matrix M

Figure 18:
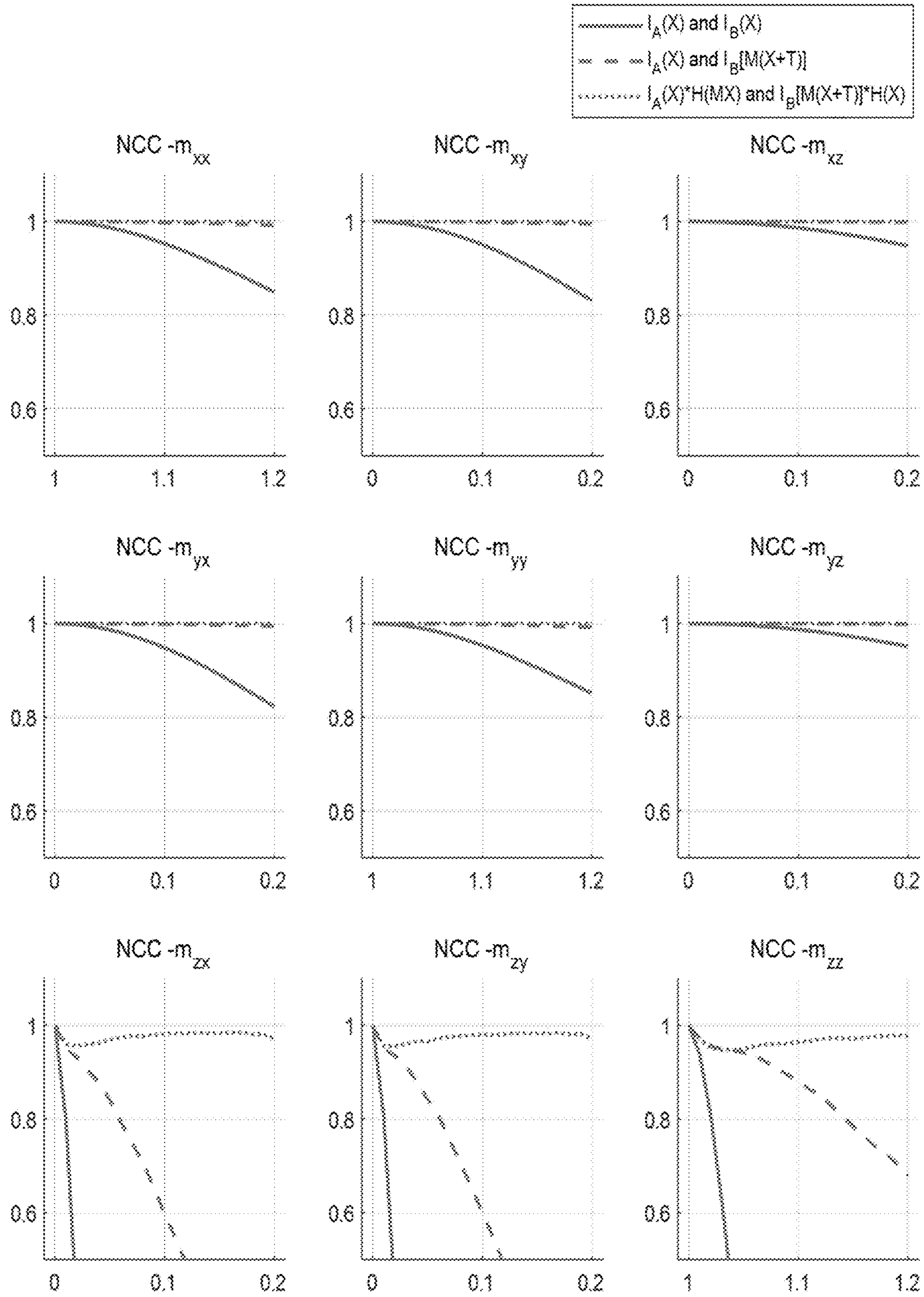
FIG. 18 shows graphs illustrating Normalized Correlation Coefficient (NCC) of images based on different motion parameters used in FastCF, in accordance with an embodiment.

In this subsection, the effect of the three parameters in M (as defined in Equation (5)) is studied. Firstly, the image model in Equation (1) is used and the scatterer-density requirement as defined in Equation (8) is applied to generate the pre and post deformation images with different motion matrices M. Then, 27 blocks are evenly selected and their normalized correlation coefficient (NCC) is averaged out to plot the curves between the NCC and the nine motion parameters in M separately. The result is shown on FIG. 18. With reference to FIG. 18, it is observed that the results are consistent with the Equation (8), i.e., if there are only small shifts along $m_{x*}$ and $m_{y*}$, while $m_{z*}$ does not change, $I_A(X)$ and $I_B$ [M(X+T)] still can achieve high correlation coefficient.

Study of Search Space and Post-Processing

Further, in this experiment, four options were tested without post-processing, i.e. "veryslow" to "medium", to study the effect of different search spaces of M and T. The running time of these options are 434.607 s, 83.928 s, 15.796 s, 2.571 s and 2.589 s respectively. For comparison purposes, the FastCF, i.e. the "medium" setting with post-processing, is also included in this experiment. FIG. 19 shows the errors across six scales using five options. Compared to the "medium" setting without post-processing, the slower options achieve lower SRMSE but show diminishing returns. On the other hand, FastCF is able to achieve similar accuracy as other slower options and runs nearly as fast as the "medium" option.

Figure 20:
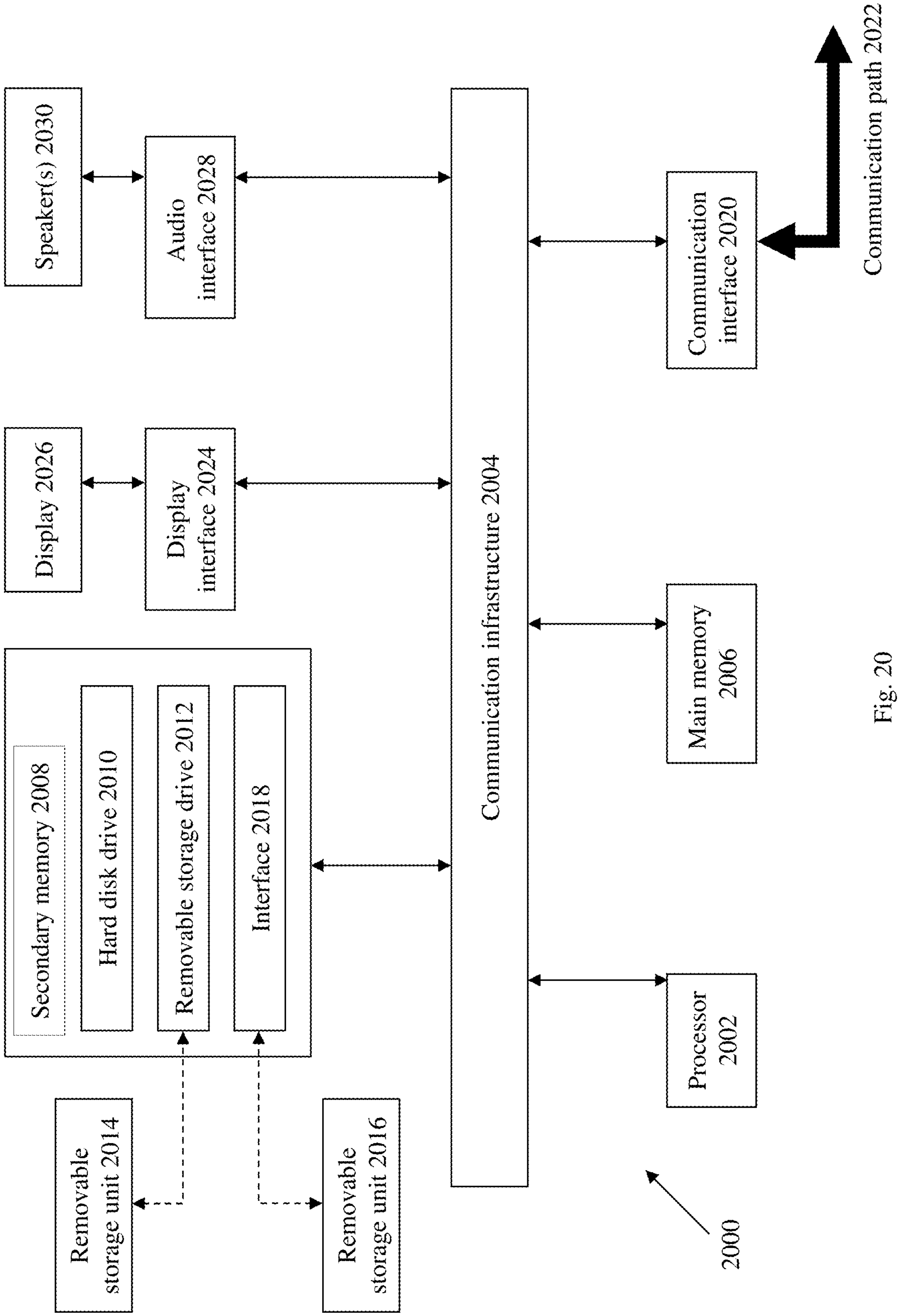
FIG. 20 shows a schematic diagram of an example of a computing device used to realise a system for performing an accelerated coupled filtering method for tissue deformation analysis, in accordance with an embodiment.

FIG. 20 depicts an exemplary computing device 2000, hereinafter interchangeably referred to as a computer system 2000. The following description of the computing device 2000 is provided by way of example only and is not intended to be limiting.

As shown in FIG. 20, the example computing device 2000 includes a processor 2002 for executing software routines. Although a single processor is shown for the sake of clarity, the computing device 2000 may also include a multiprocessor system. The processor 2002 is connected to a communication infrastructure 2004 for communication with other components of the computing device 2000. The communication infrastructure 2004 may include, for example, a communications bus, cross-bar, or network.

The computing device 2000 further includes a main memory 2006, such as a random access memory (RAM), and a secondary memory 2008. The secondary memory 2008 may include, for example, a hard disk drive 2010 and/or a removable storage drive 2012, which may include a floppy disk drive, a magnetic tape drive, an optical disk drive, or the like. The removable storage drive 2012 reads from and/or writes to a removable storage unit 2014 in a well-known manner. The removable storage unit 2014 may include a floppy disk, magnetic tape, optical disk, or the like, which is read by and written to by removable storage drive 2012. As will be appreciated by persons skilled in the relevant art(s), the removable storage unit 2014 includes a computer readable storage medium having stored therein computer executable program code instructions and/or data.

In an alternative implementation, the secondary memory 2008 may additionally or alternatively include other similar means for allowing computer programs or other instructions to be loaded into the computing device 2000. Such means can include, for example, a removable storage unit 2016 and an interface 2018. Examples of a removable storage unit 2016 and interface 2018 include a program cartridge and cartridge interface (such as that found in video game console devices), a removable memory chip (such as an EPROM or PROM) and associated socket, and other removable storage units 2016 and interfaces 2018 which allow software and data to be transferred from the removable storage unit 2016 to the computer system 2000.

The computing device 2000 also includes at least one communication interface 2020. The communication interface 2020 allows software and data to be transferred between computing device 2000 and external devices via a communication path 2022. In various embodiments of the inventions, the communication interface 2020 permits data to be transferred between the computing device 2000 and a data communication network, such as a public data or private data communication network. The communication interface 2020 may be used to exchange data between different computing devices 2000 which such computing devices 2000 form part an interconnected computer network. Examples of a communication interface 2020 can include a modem, a network interface (such as an Ethernet card), a communication port, an antenna with associated circuitry and the like. The communication interface 2020 may be wired or may be wireless. Software and data transferred via the communication interface 2020 are in the form of signals which can be electronic, electromagnetic, optical or other signals capable of being received by communication interface 2020. These signals are provided to the communication interface via the communication path 2022.

As shown in FIG. 20, the computing device 2000 further includes a display interface 2024 which performs operations for rendering images to an associated display 2026 and an audio interface 2028 for performing operations for playing audio content via associated speaker(s) 2030.

As used herein, the term "computer program product" may refer, in part, to removable storage unit 2014, removable storage unit 2016, a hard disk installed in hard disk drive 2010, or a carrier wave carrying software over communication path 2022 (wireless link or cable) to communication interface 2020. Computer readable storage media refers to any non-transitory tangible storage medium that provides recorded instructions and/or data to the computing device 2000 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computing device 2000. Examples of transitory or non-tangible computer readable transmission media that may also participate in the provision of software, application programs, instructions and/or data to the computing device 2000 include radio or infra-red transmission channels as well as a network connection to another computer or networked device, and the Internet or Intranets including e-mail transmissions and information recorded on Websites and the like.

The computer programs (also called computer program code) are stored in main memory 2006 and/or secondary memory 2008. Computer programs can also be received via the communication interface 2020. Such computer programs, when executed, enable the computing device 2000 to perform one or more features of embodiments discussed herein. In various embodiments, the computer programs, when executed, enable the processor 2002 to perform features of the above-described embodiments. Accordingly, such computer programs represent controllers of the computer system 2000.

Software may be stored in a computer program product and loaded into the computing device 2000 using the removable storage drive 2012, the hard disk drive 2010, or the interface 2018. Alternatively, the computer program product may be downloaded to the computer system 2000 over the communications path 2022. The software, when executed by the processor 2002, causes the computing device 2000 to perform functions of embodiments described herein.

It is to be understood that the embodiment of FIG. 20 is presented merely by way of example. Therefore, in some embodiments one or more features of the computing device 2000 may be omitted. Also, in some embodiments, one or more features of the computing device 2000 may be combined together. Additionally, in some embodiments, one or more features of the computing device 2000 may be split into one or more component parts.

It will be appreciated that the elements illustrated in FIG. 20 function to provide means for performing the various functions and operations of the servers as described in the above embodiments.

In an implementation, a server may be generally described as a physical device comprising at least one processor and at least one memory including computer program code. The at least one memory and the computer program code are configured to, with the at least one processor, cause the physical device to perform the requisite operations.

When the computing device 2000 is configured to realise the system 700 for performing an accelerated coupled filtering method for tissue deformation analysis, the system 700 can have a non-transitory computer readable medium having stored thereon an application which when executed causes the system 700 to perform the accelerated coupled filtering method 800 described above and/or any other methods described herein.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

What is claimed is:

1. A method for performing a tissue deformation analysis of a tissue, the method comprising:

using ultrasound imaging to image the tissue before deformation to thereby yield a pre-deformation image;

using ultrasound imaging to image the tissue after deformation to thereby yield a post-deformation image;

executing, by a processing device, a process for determining an affine motion matrix from the pre-deformation and post-deformation images;

determining, by the processing device, a displacement vector according to the pre-deformation image, post-deformation image and affine motion matrix; and estimating, by the processing device, a strain distribution of the tissue for the tissue deformation analysis according to the pre-deformation image, post-deformation image, affine motion matrix and displacement vector;

wherein the process for determining the affine motion matrix comprises:

applying a first filter on the pre-deformation image to obtain a filtered pre-deformation image;

applying a second filter on the post-deformation image to obtain a filtered post-deformation image, wherein the filtered pre-deformation image and the filtered post-deformation image are correlated by a first motion matrix comprising a plurality of first motion parameters, the first motion matrix being the affine motion matrix, wherein the plurality of first motion parameters comprise at least three fundamental first motion parameters, each of the three fundamental first motion parameters represents movement of the tissue along an axial direction relative to the axial direction, an elevational direction and a lateral direction, respectively;

estimating a respective value for each of the plurality of first motion parameters, wherein each of the estimated respective values represents a difference between the filtered pre-deformation image and the filtered post-deformation image;

in response to determining that at least one of the estimated respective values meets at least one predefined criterion, updating the at least one of the estimated respective values as an optimal value for at least one corresponding first motion parameter of the plurality of first motion parameters; and after applying the second filter, spatially transforming the post-deformation image based at least on a second motion matrix, wherein the first motion matrix is a modified version of the second motion matrix;

wherein estimating the respective values comprises:

(A) flattening a first and second plurality of voxels surrounding each of one or more pre-deformation points of interest in the filtered pre-deformation image and each of one or more post-deformation points of interest in the filtered post-deformation image, respectively, wherein the flattening is performed along the elevational direction of each of the first and second plurality of voxels, and wherein the flattening reduces the plurality of first and second motion parameters;

wherein estimating the respective values is performed in a plurality of iterations by a coarse-to-fine multi-scale strategy, each iteration adopting a scale in resolution; and wherein:

in a first iteration of the plurality of iterations:

the plurality of first motion parameters comprise two of the three fundamental first motion parameters representing movement of the tissue along the axial direction relative to the axial direction and the lateral direction, respectively; and the remaining fundamental first motion parameter is removed by the flattening; and between a second iteration to a final iteration of the plurality of iterations:

the plurality of first motion parameters comprise the two of the three fundamental first motion parameters, two lateral first motion parameters representing movement of the tissue along the lateral direction relative to the lateral direction and the elevational direction, respectively, and two axial first motion parameters representing movement of the tissue along the elevational direction relative to the lateral direction and the elevational direction, respectively.

2. The method of claim 1, wherein the process for determining the affine motion matrix further comprises:

detecting one or more envelopes present in the filtered pre-deformation image and filtered post-deformation image to obtain a filtered B-mode pre-deformation image and a filtered B-mode post-deformation image.

3. The method of claim 1, wherein applying the first filter and the second filter comprises convolving a first point spread function and second point spread function of an ultrasound system with the pre-deformation image and the post-deformation image, respectively, and wherein the first point spread function is a modified version of the second point spread function.

4. The method of claim 1, wherein the second motion matrix comprises a plurality of second motion parameters, and wherein estimating the respective values further comprises:

(B) searching, a value of each of the plurality of first motion parameters for each of the one or more pre-deformation points of interest in the filtered pre-deformation image;

(C) searching, by the processing device, a value of each of the plurality of second motion parameters for each of the one or more post-deformation points of interest in the filtered post-deformation image;

(D) generating one or more pre-deformation voxels based on the searched value of each of the plurality of first motion parameters;

(E) generating, by the processing device, one or more post-deformation voxels based on the searched value of each of the plurality of second motion parameters;

(F) calculating a similarity metric based on one or more first voxels surrounding the one or more pre-deformation voxels and one or more second voxels surrounding the one or more post-deformation voxels, wherein the similarity metric defines a similarity between a target pre-deformation point of interest and a post-deformation point of interest corresponding to the target pre-deformation point of interest; and (G) determining if the target pre-deformation point of interest matches the corresponding post-deformation point of interest based on the calculated similarity metric.

5. The method of claim 4, wherein the plurality of second motion parameters comprise at least two fundamental second motion parameters, two lateral second motion parameters and two elevational motion parameters, and wherein estimating the respective values comprises:

in the first iteration:

determining a value of each of the two of the three fundamental first motion parameters based on steps (A) to (G); between the second iteration to a third final iteration:

determining, by the processing device, an updated value of each of the two of the three fundamental first motion parameters based on steps (A) to (G); and assigning a value of each of the two lateral second motion parameters and the two elevational second motion parameters searched in step (C) in a previous iteration as a respective value of each of the two lateral first motion parameters and the two elevational first motion parameters; and in final two iterations:

assigning the determined updated value of each of the two of the three fundamental first motion parameters in the third final iteration as an optimal value of each of the two of the three fundamental first motion parameters; and assigning an updated value of each of the two lateral second motion parameters and the two elevational second motion parameters searched in step (C) in the third final iteration as an optimal value of each of the two lateral first motion parameters and the two elevational first motion parameters.

6. The method of claim 5, wherein the similarity metric comprises any one of a Normalized Correlation Coefficient, Sum of Absolute Differences and Sum of Squared Differences.

7. The method of claim 1, wherein the process for determining the affine motion matrix further comprises:

imposing an upper limit and a lower limit on a gradient of a displacement range of the fundamental first motion parameters along the axial direction, wherein values falling outside the displacement range are determined to be a wrong value of the fundamental first motion parameters;

in response to determining that one or more voxels comprise the wrong value of the fundamental first motion parameters:

determining a corrected value of the fundamental first motion parameters of the one or more voxels, wherein the corrected value is determined by interpolating the wrong value based on a predetermined correct value of the fundamental first motion parameters of voxels surrounding the one or more voxels.

8. A system for performing a tissue deformation analysis of a tissue, the system comprising:

an ultrasound system configured to image, by using ultrasound imaging, the tissue before and after deformation to thereby yield a pre-deformation image and a post-deformation image, respectively; and a processing device configured to:

execute a process for determining an affine motion matrix from the pre- deformation and post-deformation images;

determine a displacement vector according to the pre-deformation image, post-deformation image and affine motion matrix; and estimate a strain distribution of the tissue for the tissue deformation analysis according to the pre-deformation image, post-deformation image, affine motion matrix and displacement vector;

wherein the process for determining the affine motion matrix comprises:

applying a first filter on the pre-deformation image to obtain a filtered pre-deformation image;

applying a second filter on the post-deformation image to obtain a filtered post-deformation image, wherein the filtered pre-deformation image and the filtered post-deformation image are correlated by a first motion matrix comprising a plurality of first motion parameters, the first motion matrix being the affine motion matrix, wherein the plurality of first motion parameters comprise at least three fundamental first motion parameters, and wherein each of the three fundamental first motion parameters represents movement of the tissue along an axial direction relative to the axial direction, an elevational direction and a lateral direction, respectively;

estimating a respective value for each of the plurality of first motion parameters, wherein each of the estimated respective values represent a difference between the filtered pre-deformation image and the filtered post-deformation image;

in response to determining that at least one of the estimated respective values meets at least one predefined criterion, updating the at least one of the estimated respective values as an optimal value for at least one corresponding first motion parameter of the plurality of first motion parameters; and after applying the second filter, spatially transforming the post-deformation image based at least on a second motion matrix, wherein the first motion matrix is a modified version of the second motion matrix;

wherein estimating the respective values comprises:

(A) flattening a first and second plurality of voxels surrounding each of one or more pre-deformation points of interest in the filtered pre-deformation image and each of one or more post-deformation points of interest in the filtered post-deformation image, respectively, wherein the flattening is performed along the elevational direction of each of the first and second plurality of voxels, and wherein the flattening reduces the plurality of first and second motion parameters;

wherein estimating the respective values is performed in a plurality of iterations by a coarse-to-fine multi-scale strategy, each iteration adopting a scale in resolution; and wherein:

in a first iteration of the plurality of iterations:

the plurality of first motion parameters comprise two of the three fundamental first motion parameters representing movement of the tissue along the axial direction relative to the axial direction and the lateral direction, respectively; and the remaining fundamental first motion parameter is removed by the flattening; and between a second iteration to a final iteration of the plurality of iterations:

the plurality of first motion parameters comprise the two of the three fundamental first motion parameters, two lateral first motion parameters representing movement of the tissue along the lateral direction relative to the lateral direction and the axial direction, respectively, and two elevational first motion parameters representing movement of the tissue along the elevational direction relative to the lateral direction and the axial direction, respectively.

9. The system of claim 8, wherein the process for determining the affine motion matrix further comprises:

detecting one or more envelopes present in the filtered pre-deformation image and filtered post-deformation image to obtain a filtered B-mode pre-deformation image and a filtered B-mode post-deformation image.

10. The system of claim 8, wherein applying the first filter and the second filter comprises convolving a first point spread function and second point spread function of the ultrasound system with the pre-deformation image and the post-deformation image, respectively, and wherein the first point spread function is a modified version of the second point spread function.

11. The system of claim 8, wherein the second motion matrix comprises a plurality of second motion parameters, and wherein estimating the respective values further comprises:

(B) searching a value of each of the plurality of first motion parameters for each of the one or more pre-deformation points of interest in the filtered pre-deformation image;

(C) searching a value of each of the plurality of second motion parameters for each of the one or more post-deformation points of interest in the filtered post-deformation image;

(D) generating one or more pre-deformation voxels based on the searched value of each of the plurality of first motion parameters;

(E) generating one or more post-deformation voxels based on the searched value of each of the plurality of second motion parameters;

(F) calculating a similarity metric based on one or more first voxels surrounding the one or more pre-deformation voxels and one or more second voxels surrounding the one or more post-deformation voxels, wherein the similarity metric defines a similarity between a target pre-deformation point of interest and a post-deformation point of interest corresponding to the target pre-deformation point of interest; and (G) determining if the target pre-deformation point of interest matches the corresponding post-deformation point of interest based on the calculated similarity metric.

12. The system of claim 11, wherein the plurality of second motion parameters comprise at least two fundamental second motion parameters, two lateral second motion parameters and two elevational motion parameters, and wherein estimating the respective values further comprises:

in the first iteration:

determining a value of each of the two of the three fundamental first motion parameters based on steps (A) to (G);

between the second iteration to a third final iteration:

determining an updated value of each of the two of the three fundamental first motion parameters based on steps (A) to (G); and assigning a value of each of the two lateral second motion parameters and the two elevational second motion parameters searched in step (C) in a previous iteration as a respective value of each of the two lateral first motion parameters and the two elevational first motion parameters; and in final two iterations:

assigning the determined updated value of each of the two of the three fundamental first motion parameters in the third final iteration as an optimal value of each of the two of the three fundamental first motion parameters; and assigning an updated value of each of the two lateral second motion parameters and the two elevational second motion parameters searched in step (C) in the third final iteration as an optimal value of each of the two lateral first motion parameters and the two elevational first motion parameters.

13. The system of claim 12, wherein the similarity metric comprises any one of a Normalized Correlation Coefficient, Sum of Absolute Differences and Sum of Squared Differences.

14. The system of claim 8, wherein the process for determining the affine motion matrix further comprises:

imposing an upper limit and a lower limit on a gradient of a displacement range of the fundamental first motion parameters along the axial direction, wherein values falling outside the displacement range are determined to be a wrong value of the fundamental first motion parameters;

in response to determining that one or more voxels comprise the wrong value of the fundamental first motion parameters:

determining a corrected value of the fundamental first motion parameters of the one or more voxels, wherein the corrected value is determined by interpolating the wrong value based on a predetermined correct value of the fundamental first motion parameters of voxels surrounding the one or more voxels.

* * * * *